United States Patent
Iwai et al.

(10) Patent No.: US 11,067,533 B2
(45) Date of Patent: Jul. 20, 2021

(54) MANUFACTURING METHOD FOR SENSOR ELEMENT

(71) Applicant: NGK INSULATORS, LTD., Aichi (JP)

(72) Inventors: Shiho Iwai, Nagoya (JP); Takeya Miyashita, Kasugai (JP)

(73) Assignee: NGK INSULATORS, LTD., Nagoya (JP)

( * ) Notice: Subject to any disclaimer, the term of this patent is extended or adjusted under 35 U.S.C. 154(b) by 197 days.

(21) Appl. No.: 16/251,148

(22) Filed: Jan. 18, 2019

(65) Prior Publication Data

US 2019/0154629 A1 May 23, 2019

Related U.S. Application Data

(63) Continuation of application No. PCT/JP2017/026341, filed on Jul. 20, 2017.

(30) Foreign Application Priority Data

Jul. 21, 2016 (JP) .............................. JP2016-143044

(51) Int. Cl.
*G01N 27/419* (2006.01)
*G01N 27/416* (2006.01)
(Continued)

(52) U.S. Cl.
CPC ....... *G01N 27/419* (2013.01); *G01N 27/4072* (2013.01); *G01N 27/4077* (2013.01); *G01N 27/416* (2013.01); *G01N 33/0037* (2013.01)

(58) Field of Classification Search
CPC ............. G01N 27/419; G01N 27/4072; G01N 27/4077
See application file for complete search history.

(56) References Cited

U.S. PATENT DOCUMENTS 6,475,317 B1 * 11/2002 Baba ....................... B32B 18/00
156/89.12
2002/0063059 A1 * 5/2002 Sugiyama .......... G01N 27/4067
204/426
(Continued)

FOREIGN PATENT DOCUMENTS

JP  2004-294455 A  10/2004
JP  2005-510713 A   4/2005
(Continued)

OTHER PUBLICATIONS

International Preliminary Report on Patentability received in corresponding International Application No. PCT/JP2017/026341 dated Jan. 31, 2019.
(Continued)

*Primary Examiner* — Alex B Efta
(74) *Attorney, Agent, or Firm* — Mattingly & Malur, PC

(57) ABSTRACT

A manufacturing method for a sensor element includes a forming step. The forming step includes: a step (a) of forming an unfired electrode on one of plural green sheets; a step (b) of forming an unfired electrode lead and an unfired lead insulating layer on the same green sheet as in the step (a), the unfired electrode lead and to be connected to the unfired electrode, the unfired lead insulating layer surrounding at least part of the unfired electrode lead; and a step (c) of forming an unfired bonding layer so as to fill at least part of a region without the unfired lead insulating layer on the green sheet subjected to the step (b) and so as to overlap at least part of an edge portion of the unfired lead insulating layer.

7 Claims, 7 Drawing Sheets

(51) Int. Cl.
    *G01N 27/407*     (2006.01)
    *G01N 33/00*     (2006.01)

(56) References Cited

U.S. PATENT DOCUMENTS

| | | | |
|---|---|---|---|
| 2004/0094834 A1* | 5/2004 | Jun | H01L 23/49822 257/700 |
| 2005/0145492 A1 | 7/2005 | Strohmaier et al. | |
| 2006/0185978 A1* | 8/2006 | Nagao | G01N 27/4071 204/424 |
| 2008/0099126 A1* | 5/2008 | Yasuda | C04B 35/6342 156/89.12 |
| 2009/0211906 A1* | 8/2009 | Sugaya | G01N 27/4075 204/424 |
| 2014/0190827 A1 | 7/2014 | Kamada et al. | |

FOREIGN PATENT DOCUMENTS

| | | |
|---|---|---|
| JP | 2005-135869 A | 5/2005 |
| JP | 2014-010126 A | 1/2014 |
| JP | 2015-180867 A | 10/2015 |
| JP | 2015-227896 A | 12/2015 |

OTHER PUBLICATIONS

International Search Report of PCT/JP2017/026341 dated Sep. 19, 2017.

* cited by examiner

MANUFACTURING METHOD FOR SENSOR ELEMENT

CROSS-REFERENCE TO RELATED APPLICATION

This application is a continuation application of PCT/JP2017/026341, filed on Jul. 20, 2017, which claims the benefit of priority of Japanese Patent Application No. 2016-143044, filed on Jul. 21, 2016, the entire contents of which are incorporated herein by reference.

BACKGROUND OF THE INVENTION

1. Field of the Invention

The present invention relates to a manufacturing method for a sensor element.

2. Description of the Related Art

Hitherto, a gas sensor including a sensor element which detects the concentration of a specified gas, such as NOx, contained in a measurement-object gas, such as automobile exhaust gas, is known. For example, PTL 1 discloses a sensor element including plural oxygen-ion-conductive solid electrolyte layers, an outer pump electrode disposed on the top layer of a solid electrolyte layer, a measuring electrode disposed within a solid electrolyte layer, and a lead line connected to these electrodes. In this sensor element, the NOx concentration is detected in the following manner. A measurement-object gas is supplied to the vicinity of the measuring electrode, and oxygen is generated when NOx contained in the gas is reduced. Based on a current flowing between the outer pump electrode and the measuring electrode when pumping out oxygen, the NOx concentration is detected. PTL 1 also discloses a manufacturing method for the sensor element. First, plural green sheets are prepared, and predetermined patterns of electrodes, for example, are printed on the green sheets and dried. Then, the plural green sheets are stacked on each other to form a multilayer body. The multilayer body is cut in units of sensor elements, and the divided sensor element units are fired. As a result, sensor elements are produced.

It is also known that, to insulate a lead within a sensor element from a solid electrolyte layer, an insulating layer is formed on the surface of the solid electrolyte layer and the lead is formed on the insulating layer (PTL 2, for example).

CITATION LIST

Patent Literature

PTL 1: JP 2015-180867
PTL 2: JP 2015-227896

SUMMARY OF THE INVENTION

In PTL 2, the insulating layer almost entirely covers the solid electrolyte layer, and then, the lead is formed on the insulating layer. However, due to some reasons, such as the absence of oxygen ion conductivity of an insulating layer, it may be desirable to dispose the insulating layer only around a lead. To manufacture such a sensor element, a lead and an insulating layer may be formed, as shown in FIGS. 10A to 10D. On a green sheet 701 to be formed into a solid electrolyte layer, an unfired lead 791 is formed and an unfired insulating layer 792 is formed to surround the unfired lead 791 (FIG. 10A). Then, an unfired bonding layer 794 is formed on the green sheet 701 other than the area where the unfired insulating layer 792 is formed (FIG. 10B). Then, another green sheet 702 having an unfired back-surface bonding layer 797 on its bottom surface is stacked on the green sheet 701 so as to form a multilayer body (FIG. 10C). The multilayer body is then fired. As a result, a sensor element including a lead 691 formed from the unfired lead 791, an insulating layer 692 formed from the unfired insulating layer 792, and a bonding layer 694 formed from the unfired bonding layer 794 and the unfired back-surface bonding layer 797 is fabricated (FIG. 10D). As shown in FIG. 10B, the unfired insulating layer 792 is formed only around the unfired lead 791 on the green sheet 701, and the unfired bonding layer 794 is formed on the portion of the green sheet 701 without the unfired insulating layer 792. It is thus possible to fabricate a sensor element while making the height of the pattern formed on the green sheet 701 uniform.

In this manufacturing method, however, gaps 799 are produced between the unfired insulating layer 792 and the unfired bonding layer 794 in the multilayer body, as shown in FIG. 10C. In the sensor element subjected to firing, the gaps 799 may still remain between the insulating layer 692 and the bonding layer 694. With the presence of the gaps 799 in the sensor element, oxygen within the gaps 799 may flow and reach the vicinity of the electrode during the use of the sensor element, and the concentration of a specified gas may not be detected with high precision.

The present invention has been made to solve the above-described problem. It is a main object of the present invention to suppress in the precision in detecting the concentration of a specified gas in a sensor element.

To achieve the above-described main object, the present invention employs the following configurations.

A manufacturing method for a sensor element according to the present invention is a manufacturing method for a sensor element which detects the concentration of a specified gas contained in a measurement-object gas. The manufacturing method includes: a preparing step of preparing a plurality of green sheets made of ceramic, which is an oxygen-ion-conductive solid electrolyte, as a main constituent; a forming step including a step (a) of forming an unfired electrode made of a conductive paste on one of the plurality of green sheets, a step (b) of forming an unfired electrode lead and an unfired lead insulating layer on the same green sheet as in the step (a), the unfired electrode lead made of a conductive paste and to be connected to the unfired electrode, the unfired lead insulating layer made of an insulating paste and to surround at least part of the unfired electrode lead, and a step (c) of forming an unfired bonding layer made of a bonding paste so as to fill at least part of a region without the unfired lead insulating layer on the green sheet subjected to the step (b) and so as to overlap at least part of an edge portion of the unfired lead insulating layer; a stacking step of stacking the plurality of green sheets including the green sheet subjected to the steps (a) through (c) so as to form a multilayer body in which the unfired electrode lead is sandwiched between green sheets; a cutting step of cutting out an unfired sensor element from the multilayer body; and a firing step of firing the unfired sensor element to produce a sensor element including an electrode formed from the unfired electrode, an electrode lead formed from the unfired electrode lead, a lead insulating layer formed from the unfired lead insulating layer, and a bonding layer formed from the unfired bonding layer.

In this manufacturing method, in the step (c) of the forming step, the unfired bonding layer is formed so as to overlap at least part of the edge portion of the unfired lead insulating layer. This makes it less likely to produce gaps between the unfired lead insulating layer and the unfired bonding layer after the green sheets are stacked. It is accordingly less likely to produce gaps between a lead insulating layer and a bonding layer in a fired sensor element. It is thus less probable that oxygen in gaps will flow and reach the vicinity of an electrode during the use of the sensor element, thereby suppressing in the precision in detecting the concentration of a specified gas in the sensor element.

In the manufacturing method for a sensor element according to the present invention, in the step (c), the unfired bonding layer may be formed so that a maximum value Womax of a width of an overlapping region of the unfired lead insulating layer and the unfired bonding layer will be 20 to 140 μm. With the maximum value Womax of 20 μm or greater, it is even less likely to decrease the precision in detecting the concentration of a specified gas in the sensor element. With the maximum value Womax of 140 μm or smaller, it is possible to reduce a warpage which may occur in the sensor element during firing due to an increased width of the overlapping region, that is, a greater amount of paste applied to part of the green sheet. In this case, the maximum value Womax may be 120 μm or smaller, thereby making it possible to further reduce the occurrence of warpage in the sensor element.

In the manufacturing method for a sensor element according to the present invention, in the step (c), the unfired bonding layer may be formed so that a ratio Womax/Wi of a maximum value Womax [μm] of a width of an overlapping region of the unfired lead insulating layer and the unfired bonding layer to a width Wi [μm] of the unfired lead insulating layer in a direction perpendicular to a current flowing direction of the unfired electrode lead will be 0.04 to 0.29. With the ratio Womax/Wi of 0.04 or greater, the precision in detecting the concentration of a specified gas in the sensor element is even less likely to decrease. With the ratio Womax/Wi of 0.29 or smaller, it is possible to reduce a warpage which may occur in the sensor element during firing due to an increased width of the overlapping region, that is, a greater amount of paste applied to part of the green sheet. In this case, the ratio Womax/Wi may be 0.24 or smaller, thereby making it possible to further reduce the occurrence of warpage in the sensor element.

In the manufacturing method for a sensor element according to the present invention, the unfired lead insulating layer formed in the step (b) may include a straight portion. The straight portion is disposed such that the unfired electrode is not located on a line extending from the straight portion in a longitudinal direction. In the step (c), the unfired bonding layer may be formed to overlap, among edge portions of the straight portion along the longitudinal direction, at least an edge portion of the straight portion positioned closer to the unfired electrode. This configuration makes it less likely to produce gaps near the edge portion of the lead insulating layer closer to the electrode. This enhances the effect of minimizing a decrease in the detection precision in the sensor element.

In the manufacturing method for a sensor element according to the present invention, in the step (a), an unfired measuring electrode, which will be formed into a measuring electrode after firing, may be formed as the unfired electrode. In the step (b), an unfired measuring-electrode lead, which is connected to the unfired measuring electrode and will be formed into a measuring-electrode lead after firing, may be formed as the unfired electrode lead. It is thus less probable that oxygen in a gap will flow and reach the vicinity of the measuring electrode during the use of the sensor element. If oxygen in a gap flows and reaches the vicinity of the measuring electrode, the precision in detecting the concentration of a specified gas is more likely to decrease than when oxygen in a gap flows and reaches the vicinity of another electrode. By forming the unfired bonding layer to overlap at least part of the edge portion of the unfired lead insulating layer which surrounds at least part of the unfired measuring-electrode lead, it is even less probable that the precision in detecting the concentration of a specified gas in the sensor element will decrease.

In the manufacturing method for a sensor element according to the present invention, in the steps (a) through (c), a plurality of patterns of each of the unfired electrode, the unfired electrode lead, the unfired lead insulating layer, and the unfired bonding layer may be formed on the green sheet so that the patterns, each pattern corresponding to one sensor element, are arranged in a predetermined direction perpendicular to a longitudinal direction of the sensor element. In the cutting step, a plurality of the unfired sensor elements may be cut out from the multilayer body. In the firing step, the plurality of the unfired sensor elements may be fired to produce a plurality of the sensor elements. This configuration makes it possible to manufacture the plurality of sensor elements at one time.

In this case, in the manufacturing method for a sensor element according to the present invention, in the step (b), the plurality of patterns of the unfired lead insulating layer may be formed so that the patterns, each pattern corresponding to one sensor element, are arranged in the predetermined direction at a first pitch. In the step (c), the plurality of patterns of the unfired bonding layer may be formed so that the patterns, each pattern corresponding to one sensor element, are arranged in the predetermined direction at a second pitch which is smaller than the first pitch. When plural patterns of the unfired lead insulating layer are formed on a green sheet so that the patterns, each corresponding to one sensor element, are arranged in the predetermined direction, if the green sheet shrinks after drying, the pitch of the patterns of the unfired lead insulating layer becomes smaller. In this case, if the pitch for forming the plural patterns of the unfired lead insulating layer and that for forming the plural patterns of the unfired bonding layer are set to be the same pitch, misregistration occurs between at least some of the plural patterns of the unfired bonding layer and the corresponding patterns of the unfired lead insulating layer. When misregistration occurs, the width of the overlapping region of the unfired lead insulating layer and the unfired bonding layer deviates from a target value. It is thus more likely to manufacture sensor elements that fail to sufficiently maintain the precision in detecting the concentration of a specified gas. That is, the yield of the sensor elements is decreased. In contrast, the plural patterns of the unfired bonding layer are formed by using the second pitch, which is smaller than the first pitch for forming the patterns of the unfired lead insulating layer. Then, it is possible to reduce misregistration between the patterns of the unfired bonding layer and those of the unfired lead insulating layer after the green sheet has contracted. This reduces the difference between the actual value of the width of the overlapping region and the target value, thereby making it possible to improve the yield of the sensor elements.

DESCRIPTION OF EMBODIMENTS

Figure 1:
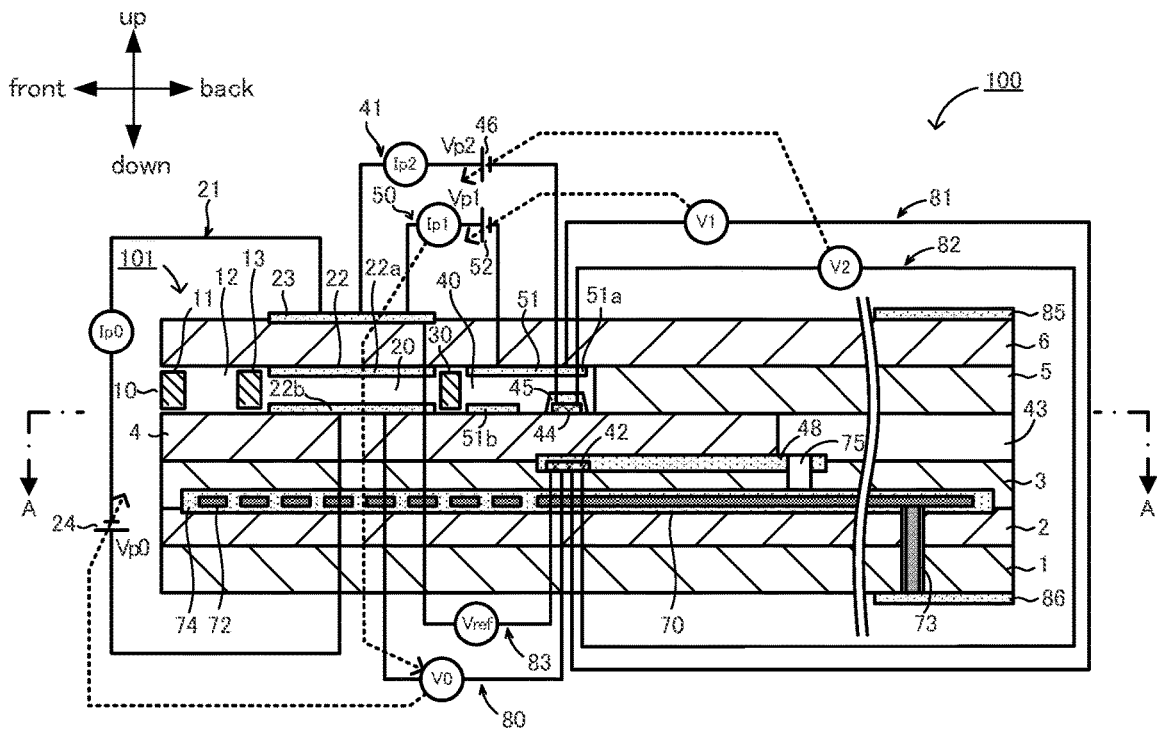
FIG. 1 is a schematic sectional view of a gas sensor 100.
Figure 2:
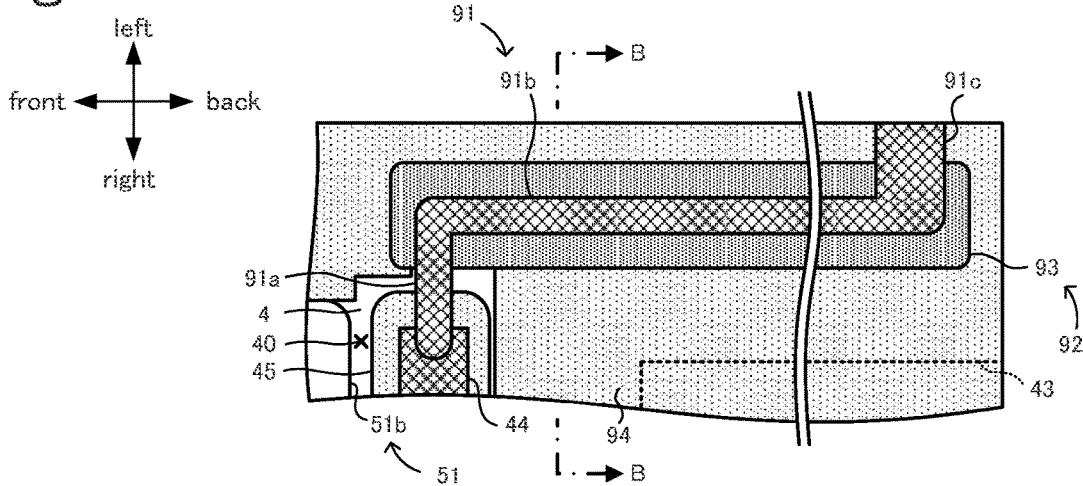
FIG. 2 is a partial sectional view taken along line A-A of FIG. 1.
Figure 3:
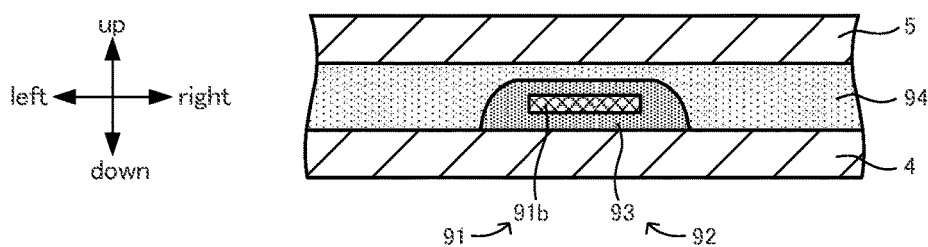
FIG. 3 is a sectional view taken along line B-B of FIG. 2.

An embodiment of the present invention will now be described below with reference to the drawings. FIG. 1 is a schematic sectional view of a gas sensor 100 including a sensor element 101 according to an embodiment of the present invention. FIG. 2 is a sectional view of a measuring electrode 44 and a measuring-electrode lead 91 and the peripheral portions thereof taken along line A-A of FIG. 1. FIG. 3 is a sectional view taken along line B-B of FIG. 2. The gas sensor 100 includes the sensor element 101 which detects the concentration of a specified gas (NOx in this embodiment) contained in a measurement-object gas. The sensor element 101 is formed in an elongated rectangular parallelepiped. The longitudinal direction (left-right direction in FIG. 1) of the sensor element 101 is set to be the front-rear direction. The thickness direction (top-bottom direction in FIG. 1) of the sensor element 101 is set to be the top-bottom direction. The width direction (perpendicular to the front-rear direction and the top-bottom direction) of the sensor element 101 is set to be the left-right direction.

The sensor element 101 includes six layers, that is, a first substrate layer 1, a second substrate layer 2, a third substrate layer 3, a first solid electrolyte layer 4, a spacer layer 5, and a second solid electrolyte layer 6, which are oxygen-ion-conductive solid electrolyte layers made of zirconia ($ZrO_2$), for example, stacked in this order from the bottom side in the drawing. The solid electrolytes forming these six layers are highly gastight. The sensor element 101 is manufactured in the following manner. After ceramic green sheets corresponding to the individual layers are subjected to certain treatment and have circuit patterns printed thereon, they are stacked on each other and are fired to be integrated with each other.

At a front end of the sensor element 101 and between the bottom surface of the second solid electrolyte layer 6 and the top surface of the first solid electrolyte layer 4, a gas inlet 10, a first diffusion controller 11, a buffer space 12, a second diffusion controller 13, a first inner space 20, a third diffusion controller 30, and a second inner space 40 are formed adjacent to each other in this order so that they can communicate with each other.

The gas inlet 10, the buffer space 12, the first inner space 20, and the second inner space 40 form a space within the sensor element 101. More specifically, assuming that the spacer layer 5 is removed from the sensor element 101, the upper portion of this space is defined by the bottom surface of the second solid electrolyte layer 6 and the lower portion of this space is defined by the top surface of the first solid electrolyte layer 4. The side portions of this space are defined by side surfaces of the spacer layer 5.

Each of the first diffusion controller 11, the second diffusion controller 13, and the third diffusion controller 30 is provided as two horizontally elongated slits (the longitudinal direction thereof is perpendicular to the plane of the drawing). The area from the gas inlet 10 to the second inner space 40 is also called a gas passage.

At a position farther away from the front end of the sensor element 101 than the gas passage, a reference gas inlet space 43 is disposed between the top surface of the third substrate layer 3 and the bottom surface of the spacer layer 5. The side portions of the reference gas inlet space 43 are defined by side surfaces of the first solid electrolyte layer 4. As a reference gas used for measuring the NOx concentration, an atmosphere, for example, is input into the reference gas inlet space 43.

An atmosphere inlet layer 48 is a layer constituted by porous ceramic. The reference gas is input into the atmosphere inlet layer 48 via the reference gas inlet space 43. The atmosphere inlet layer 48 is formed to cover a reference electrode 42.

The reference electrode 42 is formed to be sandwiched between the top surface of the third substrate layer 3 and the first solid electrolyte layer 4. As discussed above, the atmosphere inlet layer 48 which communicates with the reference gas inlet space 43 is provided around the reference electrode 42. The oxygen concentration (oxygen partial pressure) within the first inner space 20 and that within the second inner space 40 can be measured by using the reference electrode 42, which will be discussed later.

In the gas passage, the gas inlet 10 is opened to an external space. A measurement-object gas is input from the external space into the sensor element 101 via the gas inlet 10. The first diffusion controller 11 applies a predetermined diffusion resistance to the measurement-object gas input from the gas inlet 10. The buffer space 12 is provided to guide the measurement-object gas flowing from the first diffusion controller 11 to the second diffusion controller 13. The second diffusion controller 13 applies a predetermined diffusion resistance to the measurement-object gas to be input into the first inner space 20 from the buffer space 12. The measurement-object gas input from the outside of the sensor element 101 is guided to the first inner space 20 in the following manner. The measurement-object gas, which is suddenly taken into the inside of the sensor element 101 via the gas inlet 10 due to the pressure fluctuation of the measurement-object gas (exhaust pressure pulsation if the measurement-object gas is automobile exhaust gas) in the external space, is not directly guided to the first inner space 20. Instead, the measurement-object gas is guided to the first inner space 20 after the fluctuation in the concentration of the measurement-object gas has been canceled in the first diffusion controller 11, the buffer space 12, and the second diffusion controller 13. In this manner, the fluctuation in the concentration of the measurement-object gas becomes almost negligible when it is guided to the first inner space

20. The first inner space 20 is provided as a space for adjusting the oxygen partial pressure in the measurement-object gas input via the second diffusion controller 13. The oxygen partial pressure is adjusted by operating a main pump cell 21.

The main pump cell 21 is an electrochemical pump cell constituted by an inner pump electrode 22, an outer pump electrode 23, and the second solid electrolyte layer 6 sandwiched between these electrodes. The inner pump electrode 22 has a ceiling electrode portion 22a provided almost on the entire bottom surface of the second solid electrolyte layer 6 which opposes the first inner space 20. The outer pump electrode 23 is provided on the top surface of the second solid electrolyte layer 6 and in a region corresponding to the ceiling electrode portion 22a so as to be exposed to an external space.

The inner pump electrode 22 is formed so as to reach the top and bottom solid electrolyte layers (second and first solid electrolyte layers 6 and 4), which define the first inner space 20, with the spacer layer 5 interposed therebetween, which defines the side walls of the first inner space 20. More specifically, the inner pump electrode 22 is formed in the following manner. The ceiling electrode portion 22a is formed on the bottom surface of the second solid electrolyte layer 6 which serves as the ceiling surface of the first inner space 20. A bottom electrode portion 22b is formed on the top surface of the first solid electrolyte layer 4 which serves as the bottom surface of the first inner space 20. A side electrode portion (not shown) is formed on side wall surfaces (inner surfaces) of the spacer layer 5 which form both side walls of the first inner space 20. The side electrode portion is formed to connect the ceiling electrode portion 22a and the bottom electrode portion 22b. The inner pump electrode 22 is disposed so as to form a tunnel-like structure at a position where this side electrode portion is disposed.

The inner pump electrode 22 and the outer pump electrode 23 are formed as porous cermet electrodes (Pt—$ZrO_2$ cermet electrodes containing 1% of Au). The inner pump electrode 22 which contacts the measurement-object gas is made of a material having a low ability to reduce NOx components in the measurement-object gas.

In the main pump cell 21, a desired pump voltage Vp0 is applied between the inner pump electrode 22 and the outer pump electrode 23 so as to cause a pump current Ip0 to flow therebetween in the positive direction or in the negative direction. This makes it possible to pump out oxygen within the first inner space 20 to the external space or to pump oxygen within the external space into the first inner space 20.

To detect the oxygen concentration (oxygen partial pressure) in the atmosphere of the first inner space 20, an electrochemical sensor cell, that is, a main-pump-controlling oxygen partial pressure detecting sensor cell 80, is formed by the inner pump electrode 22, the second solid electrolyte layer 6, the spacer layer 5, the first solid electrolyte layer 4, the third substrate layer 3, and the reference electrode 42.

Measuring the electromotive force V0 in the main-pump-controlling oxygen partial pressure detecting sensor cell 80 makes it possible to detect the oxygen concentration (oxygen partial pressure) within the first inner space 20. As a result of feedback-controlling the pump voltage Vp0 of a variable power supply source 24 so that the electromotive force V0 becomes constant, the pump current Ip0 is controlled. This can maintain the oxygen concentration within the first inner space 20 at a predetermined constant value.

After the measurement-object gas has flown through the first inner space 20 where the oxygen concentration (oxygen partial pressure) is controlled as a result of operating the main pump cell 21, the third diffusion controller 30 applies a predetermined diffusion resistance to the measurement-object gas to guide it to the second inner space 40.

The second inner space 40 is provided as a space for performing treatment related to the measuring of the concentration of nitrogen oxide (NOx) contained in the measurement-object gas flowing from the third diffusion controller 30. The NOx concentration is mainly measured in the second inner space 40 where the oxygen concentration is controlled by an auxiliary pump cell 50 and is also measured by operating a measuring pump cell 41.

After the oxygen concentration (oxygen partial pressure) has been controlled in the first inner space 20, the oxygen partial pressure is also adjusted in the second inner space 40 by using the auxiliary pump cell 50 for the measurement-object gas flowing into the second inner space 40 via the third diffusion controller 30. This can highly precisely maintain the oxygen concentration within the second inner space 40 at a constant value, thereby achieving high-precision measurements of the NOx concentration in the gas sensor 100.

The auxiliary pump cell 50 is an auxiliary electrochemical pump cell constituted by an auxiliary pump electrode 51, the outer pump electrode 23, and the second solid electrolyte layer 6. The auxiliary pump electrode 51 has a ceiling electrode portion 51a provided almost on the entire bottom surface of the second solid electrolyte layer 6 which opposes the second inner space 40. The outer pump electrode 23 may not necessarily be used to form the auxiliary pump cell 50, and a suitable electrode outside the sensor element 101 may alternatively be used.

The auxiliary pump electrode 51 is disposed within the second inner space 40 so as to form a tunnel-like structure, as in the inner pump electrode 22 disposed within the first inner space 20. The ceiling electrode portion 51a is formed on the second solid electrolyte layer 6 which defines the ceiling surface of the second inner space 40. A bottom electrode portion 51b is formed on the first solid electrolyte layer 4 which defines the bottom surface of the second inner space 40. A side electrode portion (not shown) which interconnects the ceiling electrode portion 51a and the bottom electrode portion 51b is formed on both side wall surfaces of the spacer layer 5 which form the side walls of the second inner space 40. As well as the inner pump electrode 22, the auxiliary pump electrode 51 is made of a material having a low ability to reduce NOx components in the measurement-object gas.

In the auxiliary pump cell 50, with the application of a desired pump voltage Vp1 between the auxiliary pump electrode 51 and the outer pump electrode 23, oxygen in the atmosphere of the second inner space 40 can be pumped out to the external space or oxygen within the external space can be pumped into the second inner space 40.

To control the oxygen partial pressure in the atmosphere of the second inner space 40, an electrochemical sensor cell, that is, an auxiliary-pump-controlling oxygen partial pressure detecting sensor cell 81, is formed by the auxiliary pump electrode 51, the reference electrode 42, the second solid electrolyte layer 6, the spacer layer 5, the first solid electrolyte layer 4, and the third substrate layer 3.

The auxiliary pump cell 50 performs pumping by using a variable power supply source 52. The variable power supply source 52 is voltage-controlled based on the electromotive force V1 detected in the auxiliary-pump-controlling oxygen partial pressure detecting sensor cell 81. This makes it possible to control and reduce the oxygen partial pressure in the atmosphere of the second inner space 40 to be low enough substantially not to influence the NOx measurements.

The pump current Ip1 is also used for controlling the electromotive force of the main-pump-controlling oxygen partial pressure detecting sensor cell 80. More specifically, the pump current Ip1 is input into the main-pump-controlling oxygen partial pressure detecting sensor cell 80 as a control signal so as to control the electromotive force V0 of the main-pump-controlling oxygen partial pressure detecting sensor cell 80. The electromotive force V0 is controlled so that the slope of the oxygen partial pressure of the measurement-object gas flowing from the third diffusion controller 30 into the second inner space 40 becomes constant. If the gas sensor 100 is used as a NOx sensor, the oxygen concentration within the second inner space 40 is maintained at a constant value of about 0.001 ppm by the functions of the main pump cell 21 and the auxiliary pump cell 50.

The measuring pump cell 41 measures the NOx concentration contained in the measurement-object gas within the second inner space 40. The measuring pump cell 41 is an electrochemical pump cell constituted by the measuring electrode 44, the outer pump electrode 23, the second solid electrolyte layer 6, the spacer layer 5, and the first solid electrolyte layer 4. The measuring electrode 44 is provided on the top surface of the first solid electrolyte layer 4 at a position at which it opposes the second inner space 40 and is separated from the third diffusion controller 30.

The measuring electrode 44 is a porous cermet electrode. The measuring electrode 44 also serves as a NOx reduction catalyst for reducing NOx in the atmosphere of the second inner space 40. The measuring electrode 44 is covered with a fourth diffusion controller 45.

The fourth diffusion controller 45 is a porous ceramic film. The fourth diffusion controller 45 serves to limit the volume of NOx flowing into the measuring electrode 44 and also serves as a protection film for the measuring electrode 44. The measuring pump cell 41 can pump out oxygen generated by the decomposing of nitrogen oxide in the atmosphere around the measuring electrode 44 so as to detect the volume of generated oxygen as the pump current Ip2.

To detect the oxygen partial pressure around the measuring electrode 44, an electrochemical sensor cell, that is, a measuring-pump-controlling oxygen partial pressure detecting sensor cell 82, is formed by the first solid electrolyte layer 4, the third substrate layer 3, the measuring electrode 44, and the reference electrode 42. A variable power supply source 46 is controlled based on the electromotive force V2 detected in the measuring-pump-controlling oxygen partial pressure detecting sensor cell 82.

The measurement-object gas flowing into the second inner space 40 reaches the measuring electrode 44 via the fourth diffusion controller 45 in the state in which the oxygen partial pressure is controlled. Nitrogen oxide contained in the measurement-object gas around the measuring electrode 44 is reduced ($2NO \rightarrow N_2 + O_2$) so as to generate oxygen. The generated oxygen is pumped out by the measuring pump cell 41. When oxygen is pumped out, the voltage Vp2 of the variable power supply source 46 is controlled so that the electromotive force V2 detected in the measuring-pump-controlling oxygen partial pressure detecting sensor cell 82 becomes constant. The volume of oxygen generated around the measuring electrode 44 is proportional to the concentration of nitrogen oxide in the measurement-object gas. The concentration of nitrogen oxide in the measurement-object gas is thus calculated by using the pump current Ip2 detected by the measuring pump cell 41.

Alternatively, the measuring electrode 44, the first solid electrolyte layer 4, the third substrate layer 3, and the reference electrode 42 may be combined with each other to form an oxygen partial pressure detector as an electrochemical sensor cell. It is then possible to detect the electromotive force based on the difference between the volume of oxygen contained in the reference atmosphere and that generated by the reducing of NOx components in the atmosphere around the measuring electrode 44. This also makes it possible to detect the concentration of NOx components in the measurement-object gas.

An electrochemical sensor cell 83 is formed by the second solid electrolyte layer 6, the spacer layer 5, the first solid electrolyte layer 4, the third substrate layer 3, the outer pump electrode 23, and the reference electrode 42. By using the electromotive force Vref generated by this sensor cell 83, the oxygen partial pressure in the measurement-object gas outside the sensor can be detected.

In the gas sensor 100 configured as described above, the measurement-object gas is supplied to the measuring pump cell 41 while the oxygen partial pressure is maintained at a constant low value (which does not substantially influence the NOx measurements) by operating the main pump cell 21 and the auxiliary pump cell 50. The pump current Ip2 flows as a result of the measuring pump cell 41 pumping out oxygen generated by the NOx reduction substantially proportionally to the NOx concentration in the measurement-object gas. Based on this pump current Ip2, the NOx concentration in the measurement-object gas can be detected.

The sensor element 101 also includes a heater unit 70 to enhance the oxygen ion conductivity of the solid electrolytes. The heater unit 70 serves to adjust the temperature of the sensor element 101 by heating it and keeping it hot. The heater 70 includes a heater 72, a through-hole 73, a heater insulating layer 74, and a pressure distributing hole 75.

The heater 72 is an electric resistor sandwiched between the second substrate layer 2 and the third substrate layer 3 in the top-bottom direction. The heater 72 is connected to a lower connector pad 86 via the through-hole 73. Upon receiving power from the outside via the lower connector pad 86, the heater 72 generates heat to heat the solid electrolytes forming the sensor element 101 and to keep them hot.

The heater 72 is buried along the entirety of the first inner space 20 and that of the second inner space 40 so as to adjust the temperature of the entire sensor element 101 to a temperature at which the above-described solid electrolytes can be activated.

The heater insulating layer 74, which is an insulator made of alumina, for example, is formed on the top and bottom surfaces of the heater 72. The heater insulating layer 74 is formed to achieve electrical insulation between the second substrate layer 2 and the heater 72 and between the third substrate layer 3 and the heater 72.

The pressure distributing hole 75 is provided to pass through the third substrate layer 3 to communicate with the reference gas inlet space 43. The pressure distributing hole 75 is formed to relax an increase in the internal pressure which accompanies a temperature rise in the heater insulating layer 74.

An upper connector pad 85 (see FIG. 1) is disposed at the rear end of the top surface of the second solid electrolyte layer 6. Likewise, the lower connector pad 86 is disposed at the rear end of the bottom surface of the first substrate layer 1. The upper and lower connector pads 85 and 86 serve as connector electrodes for electrically connecting the sensor element 101 to the outside. Plural (four in this embodiment) upper connector pads 85 and plural (four in this embodiment) lower connector pads 86 are disposed, though they are not shown. One of the upper connector pads 85 is electrically connected to the measuring-electrode lead 91 shown in FIGS. 2 and 3 and is also electrically connected to the measuring electrode 44 via the measuring-electrode lead 91. Each of the electrodes other than the measuring electrode 44 is also electrically connected to the upper connector pad 85 or the lower connector pad 86 via an electrode lead, which is not shown. It is possible to apply a voltage or a current to the electrodes (inner pump electrode 22, outer pump electrode 23, reference electrode 42, measuring electrode 44, and auxiliary pump electrode 51) of the sensor element 101 from outside and to measure the voltage or the current of each of the electrodes via these upper and lower connector pads 85 and 86. Applying of a voltage by using the variable power supply sources 24, 46, and 52 and detecting of the pump currents Ip0, Ip1, and Ip2 and the electromotive forces V0, V1, V2, and Vref are also performed via these upper and lower connector pads 85 and 86.

The measuring-electrode lead 91 is a cermet conductor made of zirconia, which is the main constituent for the first solid electrolyte layer 4, and a precious metal, such as platinum, or a high melting-point metal, such as tungsten or molybdenum. As shown in FIG. 2, the measuring-electrode lead 91 is located farther leftward than the measuring electrode 44 in the sensor element 101. The measuring-electrode lead 91 includes a first straight portion 91a, a second straight portion 91b, and a third straight portion 91c. The first straight portion 91a is connected to the left side of the measuring electrode 44 and extends in the left-right direction. The second straight portion 91b is connected at its front end to the left end of the first straight portion 91a and extends in the front-rear direction. The third straight portion 91c is connected at its right end to the rear end of the second straight portion 91b and extends in the left-right direction. The third straight portion 91c is exposed at its end on the left surface of the sensor element 101, and is connected to one of the upper connector pads 85 via a side lead, which is not shown, disposed on the left surface of the sensor element 101. Most part of the measuring-electrode lead 91 is surrounded by a lead insulating layer 92 disposed on the first solid electrolyte layer 4.

The lead insulating layer 92 is an insulator made of alumina, for example, and insulates at least part of the measuring-electrode lead 91 from the first solid electrolyte layer 4 and the spacer layer 5. The lead insulating layer 92 has a straight portion 93, as shown in FIG. 2. The straight portion 93 is disposed such that its longitudinal direction matches the front-rear direction. The straight portion 93 surrounds the measuring-electrode lead 91 such that it surrounds part of the first straight portion 91a, the entirety of the second straight portion 91b, and part of the third straight portion 91c. The straight portion 93 is disposed along the second straight portion 91b, and the measuring electrode 44 is not located on a line extending from the straight portion 93 in the longitudinal direction (front-rear direction). The straight portion 93 does not cover part of the right side of the first straight portion 91a nor does it cover part of the left side of the third straight portion 91c. This configuration prevents the lead insulating layer 92 from covering portions where oxygen ion conduction or electrical connection is required, such as the second inner space 40, the measuring electrode 44, and the left side of the third straight portion 91c, during the manufacturing of the sensor element 101.

As shown in FIGS. 2 and 3, a bonding layer 94 is provided on the first solid electrolyte layer 4, though it is not shown in FIG. 1. The bonding layer 94 bonds the spacer layer 5 and the first solid electrolyte layer 4 with each other. The bonding layer 94 covers most part of the top surface of the first solid electrolyte layer 4, except for the gas passage, such as the buffer space 12, the first inner space 20, and the second inner space 40. The bonding layer 94 preferably has oxygen ion conductivity, as in the layers 1 through 6. In this embodiment, the bonding layer 94 is ceramic made of zirconia as the main constituent, as in the layers 1 through 6. A bonding layer, which is not shown, is disposed, not only between the spacer layer 5 and the first solid electrolyte layer 4, but also between adjacent layers of the layers 1 through 6.

Figure 4:
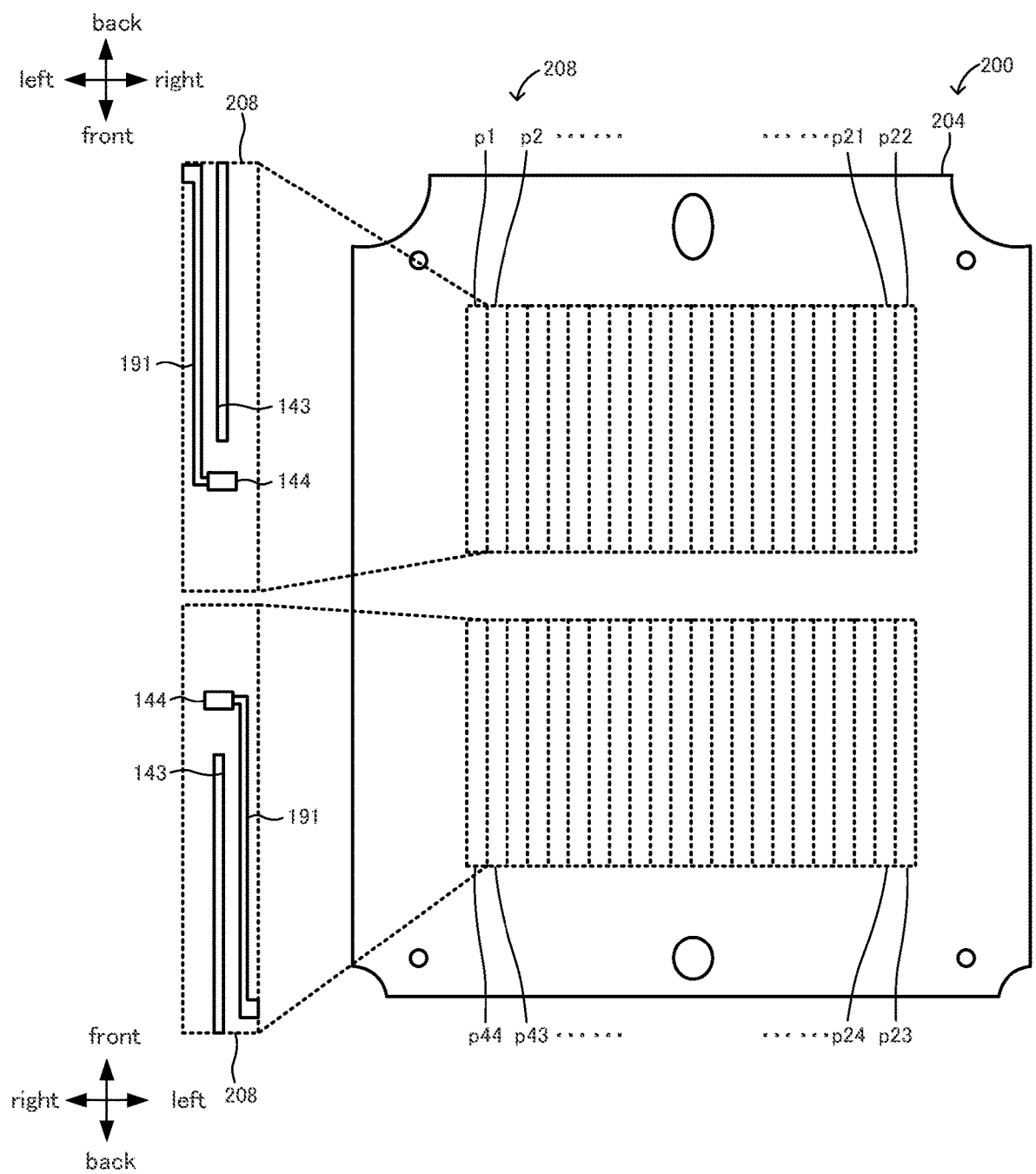
FIG. 4 is a view illustrating a green sheet 204 and plural device regions 208.
Figure 5A:
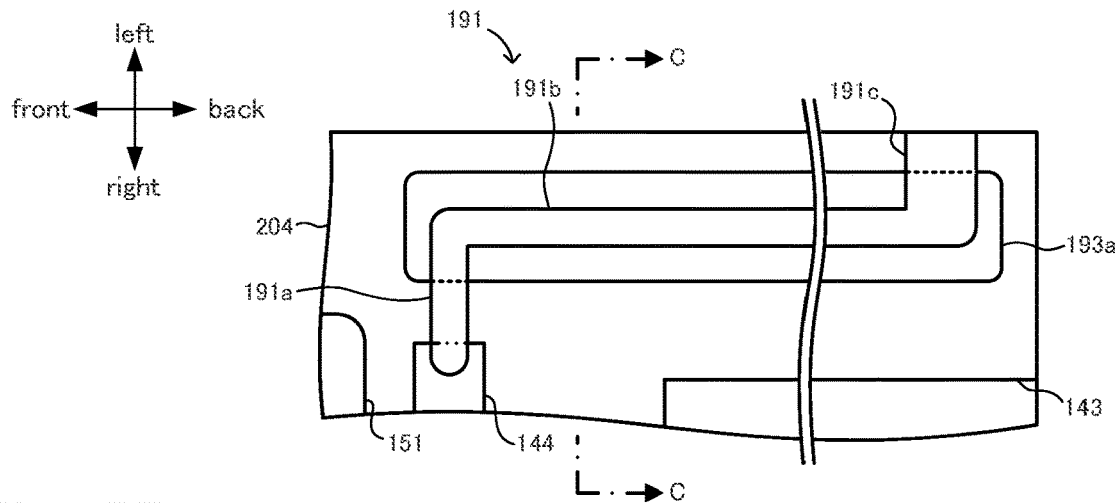
FIGS. 5A to 5C show top views illustrating that individual patterns are being formed on the green sheet 204.
Figure 5B:
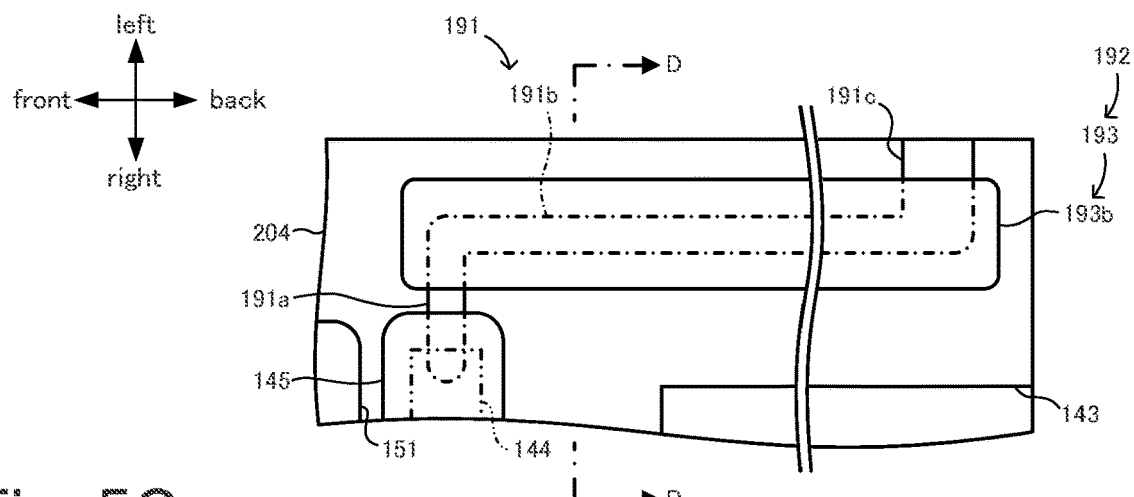
Figure 5C:
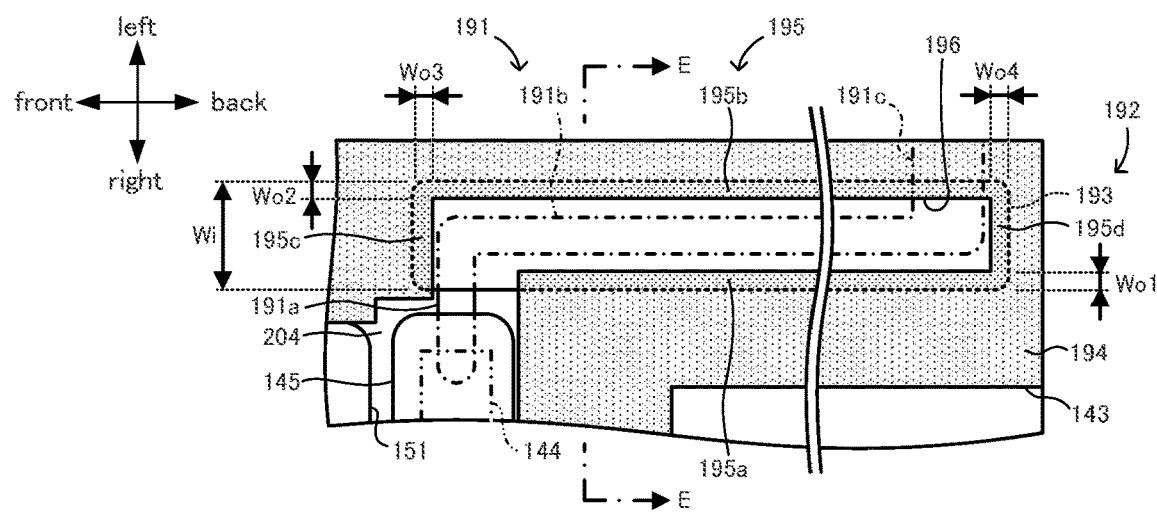
Figure 6A:
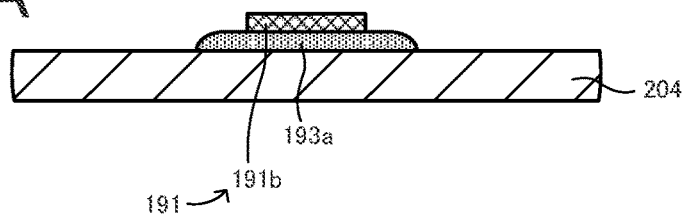
FIGS. 6A to 6F show sectional views illustrating that individual patterns are being formed on the green sheet 204.
Figure 6B:
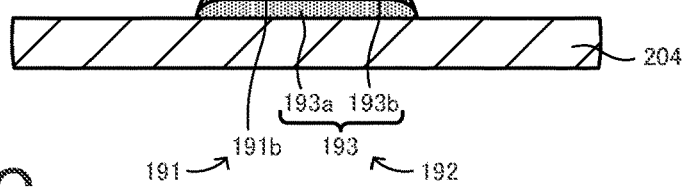
Figure 6C:
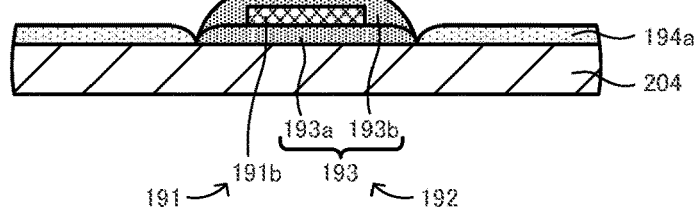
Figure 6D:
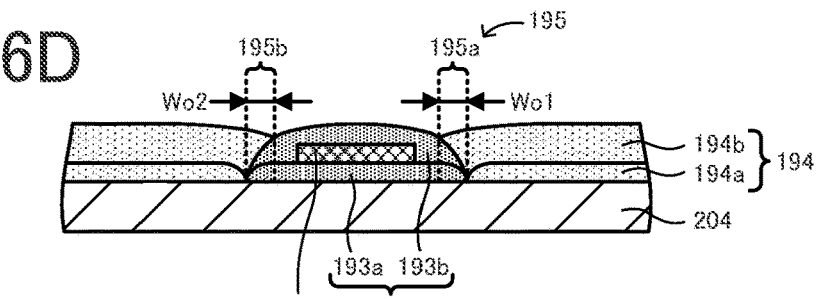

A manufacturing method for the sensor element 101 of the gas sensor 100 will now be discussed below. FIG. 4 is a view illustrating a green sheet 204 and plural device regions 208. FIGS. 5A to 5C show top views illustrating that individual patterns are being formed on the green sheet 204. FIGS. 6A to 6F shows sectional views illustrating that individual patterns are being formed on the green sheet 204. FIG. 6A is a sectional view taken along line C-C of FIG. 5A. FIG. 6B is a sectional view taken along line D-D of FIG. 5B. FIG. 6D is a sectional view taken along line E-E of FIG. 5C. FIGS. 5A to 5C shows some patterns formed in one device region 208 of the green sheet 204.

[Preparing Step]

When fabricating the sensor element 101, a preparing step is performed to prepare plural green sheets 200 made of ceramic (zirconia in this embodiment), which is an oxygen-ion-conductive solid electrolyte, as the main constituent. In this embodiment, the sensor element 101 is constituted by six layers, that is, the first through third substrate layers 1 through 3, the first solid electrolyte layer 4, the spacer layer 5, and the second solid electrolyte layer 6. Accordingly, six green sheets 200 are prepared in association with the six layers. In FIG. 4, as one of the six green sheets 200, the green sheet 204, which is formed into the first solid electrolyte layer 4 after it is fired, is shown. In the preparing step, fabricated green sheets 200 may be used, or green sheets 200 may be formed. If the green sheets 200 are formed, they may be formed in the following manner. Stabilized zirconia powder, an organic binder, a plasticizer, an organic solvent are mixed to form a paste. The green sheets 200 are formed by using this paste according to the doctor blade method. As shown in FIG. 4, the green sheet 200 is formed in a substantially rectangle. Punching, for example, is made on the green sheet 200 in advance by using a machine press to cut off the four corners in an arch-like shape and also to form sheet holes. These portions are used for forming patterns or for positioning of the layers to be stacked on each other, which will be discussed later. If a certain layer has an inner space, a space (hole) corresponding to the inner space is formed in the corresponding green sheet 200.

[Forming Step]

Then, a forming step is conducted to form patterns corresponding to each of plural sensor elements 101 on one or more plural green sheets 200 and to dry the formed patterns. Specifically, the patterns are those for the electrodes, such as the measuring electrode 44, shown in FIGS. 1 through 3, and those for forming the measuring-electrode lead 91, the lead insulating layer 92, the bonding layer 94, and the heater unit 70, for example, shown in FIGS. 1 through 3. As shown in FIG. 4, plural device regions 208, each of which is a region where the patterns corresponding to one sensor element 101 are formed, are arranged on each of the green sheets 200. Individual patterns are formed in each of the device regions 208. The plural device regions 208 are arranged in a predetermined direction (left-right direction in FIG. 4, which is the longitudinal direction of the green sheet 204) perpendicular to the longitudinal direction (front-rear direction) of the sensor element 101. In this embodiment, twenty-two device regions 208 are arranged in the predetermined direction and two rows of the twenty-two device regions 208 are arranged in a direction (longitudinal direction of the sensor element) perpendicular to the predetermined direction. That is, a total of forty-four device regions 208 are arranged. To distinguish the forty-four device regions 208 from each other, as shown in FIG. 4, the twenty-two device regions 208 in the upper section will be called device regions p1 through p22 from the left to the right in FIG. 4, and the twenty-two device regions 208 in the lower section will be called device regions p23 through p44 from the right to the left in FIG. 4. In the plural device regions 208, the orientations of the patterns to be formed are also determined. As shown in the enlarged portions in FIG. 4, the patterns in the device regions p1 through p22 in the upper section are formed such that the front side of the sensor element 101 faces downward in FIG. 4. The patterns in the device regions p23 through p44 in the lower section are formed such that the front side of the sensor element 101 faces upward in FIG. 4. In the enlarged portions in FIG. 4, to indicate the orientations of the patterns, the arrows indicating the front, rear, left, and right directions of the sensor elements 101, an unfired measuring electrode 144, which is a pattern for the measuring electrode 44, an unfired measuring-electrode lead 191, which is a pattern for the measuring-electrode lead 91, and a space 143, which is a space corresponding to the reference gas inlet space 43, are shown. The space 143 is a hole formed by punching in the above-described preparing step. The individual patterns are formed by applying pattern-forming pastes to a green sheet 200 by using a known screen printing technique. The pattern-forming pastes have been prepared in accordance with the characteristics required for the corresponding patterns to be formed.

The forming step includes the following steps (a) through (c). In step (a), the unfired measuring electrode 144 made of a conductive paste is formed on the green sheet 204, which is one of the plural green sheets 200. In step (b), the unfired measuring-electrode lead 191 and an unfired lead insulating layer 192 are formed on the same green sheet 204 as that used in step (a). The unfired measuring-electrode lead 191 is made of a conductive paste and is connected to the unfired measuring electrode 144. The unfired lead insulating layer 192 is made of an insulating paste and surrounds at least part of the unfired measuring-electrode lead 191. The unfired measuring electrode 144, the unfired measuring-electrode lead 191, and the unfired lead insulating layer 192 will respectively be formed into the measuring electrode 44, the measuring-electrode lead 91, and the lead insulating layer 92 after they are fired. In accordance with the positions and configurations shown in FIGS. 1 through 3, the unfired measuring electrode 144, the unfired measuring-electrode lead 191, and the unfired lead insulating layer 192 are formed in each of the plural device regions 208 on the green sheet 204. Specifically, steps (a) and (b) are performed in the following manner, for example. First of all, step (a) is conducted to form the unfired measuring electrode 144 on the green sheet 204. Then, step (b) is conducted. More specifically, a lower insulating layer 193a, which is part of the unfired lead insulating layer 192, is first formed, and then, the unfired measuring-electrode lead 191 is formed on the lower insulating layer 193a (FIGS. 5A and 6A). As shown in FIG. 5A, the unfired measuring-electrode lead 191 includes first through third straight portions 191a through 191c corresponding to the first through third straight portions 91a through 91c of the measuring-electrode lead 91. Then, an upper insulating layer 193b is formed on the lower insulating layer 193a and the unfired measuring-electrode lead 191 on the lower insulating layer 193a (FIGS. 5B and 6B). As a result, the unfired lead insulating layer 192 having a straight portion 193 constituted by the lower insulating layer 193a and an upper insulating layer 193b is formed. The unfired lead insulating layer 192 is formed to surround at least part of the unfired measuring-electrode lead 191. In this embodiment, the straight portion 193 is formed to surround part of the first straight portion 191a, the entirety of the second straight portion 191b, and part of the third straight portion 191c. The thickness of the unfired measuring-electrode lead 191 is about 7 to 17 μm, and the thickness of the unfired lead insulating layer 192 (total thickness of the lower insulating layer 193a and the upper insulating layer 193b) is about 20 to 40 μm, though they are not restricted to these ranges.

In this embodiment, when forming the unfired measuring electrode 144 in step (a), an unfired auxiliary pump electrode 151 (see FIG. 5A) and an unfired main pump electrode (not shown) are also formed. The unfired auxiliary pump electrode 151 will be formed into the bottom electrode portion 51b of the auxiliary pump electrode 51 after it is fired. The unfired main pump electrode will be formed into the bottom electrode portion 22b of the inner pump electrode 22 after it is fired. After the upper insulating layer 193b has been formed in step (b), an unfired fourth diffusion controller 145, which will be formed into the fourth diffusion controller 45 after it is fired, is formed (see FIG. 5B).

In step (c), an unfired bonding layer 194 made of a bonding paste is formed to fill at least part of the region without the unfired lead insulating layer 192 on the green sheet 204 subjected to step (b) and also to overlap at least part of the edge portion of the unfired lead insulating layer 192. The unfired bonding layer 194 will be formed into the bonding layer 94 (part of the bonding layer 94) after it is fired. For example, the unfired bonding layer 194 is formed as a pattern including a region where the unfired bonding layer 194 is formed (indicated by the pale hatched portion and the dense hatched portion in FIG. 5C) and a non-forming region 196 where the unfired bonding layer 194 is not formed. The non-forming region 196 includes a region where the gas passage, such as the buffer space 12, the first inner space 20, and the second inner space 40, will be formed, and part of the region where the unfired lead insulating layer 192 is formed (region other than an overlapping region 195) on the top layer of the green sheet 204. The unfired bonding layer 194 is formed to fill (cover) most part of the top surface of the green sheet 204 other than the non-forming region 196. The unfired bonding layer 194 is formed to have the overlapping region 195 (indicated by the dense hatched portion in FIG. 5C) where the unfired bonding layer 194 overlaps the edge portion of the straight portion 193 of the unfired lead insulating layer 192. As shown in FIG. 5C, the unfired bonding layer 194 is not formed in the portion of the green sheet 204 where the space 143 is formed. However, a hole (space 143) has been formed on the green sheet 204 to remove the top surface of the green sheet 204. The unfired bonding layer 194 is not required to be formed as a pattern to avoid the space 143. In this embodiment, the unfired bonding layer 194 is formed separately over multiple times (twice in this example) by printing a lower bonding layer 194a and an upper bonding layer 194b. In the first printing, the lower bonding layer 194a is formed to contact the edge portion of the unfired lead insulating layer 192 (FIG. 6C). In the second printing, the upper bonding layer 194b is formed to overlap at least part of the edge portion of the unfired lead insulating layer 192 (FIGS. 5C and 6D). As in other patterns, such as unfired measuring electrode 144, the unfired bonding layer 194 is also formed in each of the plural device regions 208 on the green sheet 204.

Specifically, the overlapping region 195 includes a first overlapping region 195a which overlaps the right-side edge portion of the straight portion 193 and a second overlapping region 195b which overlaps the left-side edge portion of the straight portion 193. The overlapping region 195 also includes a third overlapping region 195c which overlaps the front-side edge portion of the straight portion 193 and a fourth overlapping region 195d which overlaps the rear-side edge portion of the straight portion 193. The overlapping region 195 of the unfired lead insulating layer 192 and the unfired bonding layer 194 is a portion where the unfired lead insulating layer 192 and the unfired bonding layer 194 overlap each other, as viewed in a direction (as viewed from above in this embodiment) perpendicular to the surface on which they are formed (top surface of the green sheet 204). In this embodiment, the pattern configuration of the unfired lead insulating layer 192 and that of the unfired bonding layer 194 are determined so that the width Wo1 of the first overlapping region 195a will be substantially uniform at any position in the front-rear direction. Likewise, the pattern configuration of the unfired lead insulating layer 192 and that of the unfired bonding layer 194 are determined so that each of the widths Wo2 through Wo4 of the second through fourth overlapping regions 195b through 195d will be substantially uniform at any position in the corresponding direction. The pattern configuration of the unfired lead insulating layer 192 and that of the unfired bonding layer 194 are also determined so that the widths Wo1 through Wo4 will be substantially equal to each other. As discussed above, the unfired bonding layer 194 is not formed in a region where the second inner space 40 will be formed. Hence, the unfired bonding layer 194 is not formed around the right front area of the straight portion 193 (around the first straight portion 191a which is not surrounded by the unfired lead insulating layer 192 and around the unfired measuring electrode 144). In this manner, it is not necessary to form the overlapping region 195 in the area where the edge portion of the unfired bonding layer 194 and that of the unfired lead insulating layer 192 are not adjacent to each other. In this embodiment, the pattern configuration of the unfired lead insulating layer 192 and that of the unfired bonding layer 194, for example, are the same for all the device regions p1 through p44 on the green sheet 204. The thickness of the unfired bonding layer 194 (total thickness of the lower bonding layer 194a and the upper bonding layer 194b) is about 25 to 45 μm, though it is not restricted to this range. The thickness of the unfired bonding layer 194 is preferably close to (for example, 0.8 to 1.2 times as large as) the total thickness of the unfired measuring-electrode lead 191 and the unfired lead insulating layer 192.

As a result of conducting the forming step including the above-described steps (a) through (c), the patterns for each of the plural sensor elements 101 are formed in each of the plural device regions 208 arranged in each of the plural green sheets 200. The forming order of the patterns in the forming step may be changed as required as long as the required patterns are formed at the required positions. Regarding the order of steps (a) through (c), for example, step (c) is performed after step (b). Step (a) may be performed after step (c) or may alternatively be performed after step (b) and before step (c). In the forming step, after the patterns have been formed as described above, drying is conducted. Drying may be conducted by using a known drying technique. For example, drying is typically conducted in the atmosphere at a temperature of 75 to 90° C. In this embodiment, drying for a green sheet 200 is conducted after pattern formation has been performed one time. However, drying for a green sheet 200 may be conducted after pattern formation has been performed multiple times or after pattern formation has been completed.

[Stacking Step]

Figure 6E:
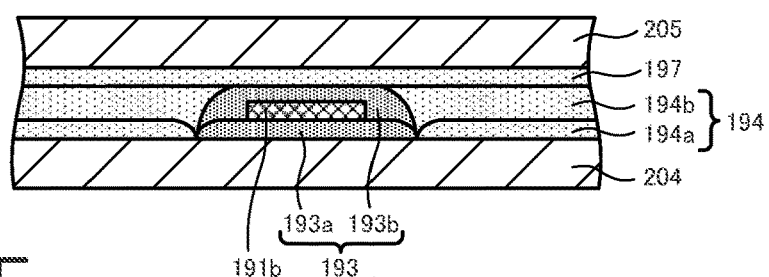

A stacking step is conducted to stack the plural green sheets 200 including the green sheet 204 subjected to steps (a) through (c) so as to form a multilayer body in which the unfired measuring-electrode lead 191 is sandwiched between green sheets 200. In this stacking step, unfired back-surface bonding layers used for bonding the plural green sheets 200 including the green sheet 204 are first formed and dried. The unfired back-surface bonding layers are formed by screen printing, for example, using a bonding-layer paste made of the same material as that of the unfired bonding layer 194, for example. The unfired back-surface bonding layer is formed by printing a bonding-layer paste on the back surface of each green sheet 200 (for example, the surface opposite the surface on which the patterns are formed in the forming step), for example, in the entire region including the plural device regions 208 (device regions p1 through p44). The thickness of the unfired back-surface bonding layer is about 7 to 17 μm, though it is not restricted to this range. Forming and drying of the unfired back-surface bonding layers may be performed in the forming step. After the unfired back-surface bonding layers are formed and dried, the plural green sheets 200 are overlaid on each other and are pressed in the top-bottom direction (thickness direction of the sheets) by using a known stacking tool while performing positioning of the plural green sheets 200 by using sheet holes formed in the green sheets 200, thereby forming a multilayer body. As a result, as shown in FIG. 6E, a pattern, such as the unfired measuring-electrode lead 191, formed on the green sheet 204 is sandwiched and pressed between the green sheet 204 and a green sheet 205 having an unfired back-surface bonding layer 197 formed on the back surface. The green sheet 205 is a sheet to be used as the spacer layer 5 after it is fired. Another green sheet 200 is stacked under the green sheet 204 and above the green sheet 205, though they are not shown in FIG. 6E.

[Cutting Step]

After forming the multilayer body in the stacking step, a cutting step is conducted to cut out plural unfired sensor elements from the multilayer body. In the cutting step, the multilayer body is cut based on the sheet holes and cut marks, which are not shown, on the green sheets 200 so as to cut out plural (forty-four in this embodiment) unfired sensor elements. In this case, cutting is conducted to cut out the device regions 208 shown in FIG. 4 in the individual green sheets 200 of the multilayer body.

[Firing Step]

Figure 6F:
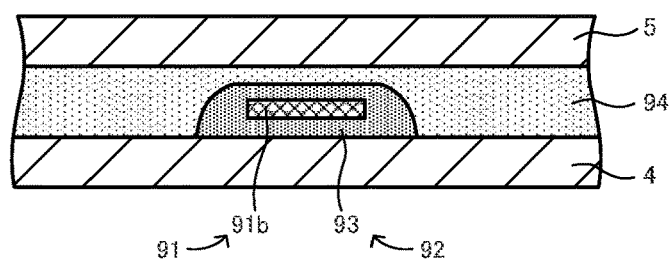

A firing step is conducted to fire the cut plural unfired sensor elements under predetermined conditions. As a result, the plural sensor elements 101 are produced. After conducting the firing step, the unfired measuring electrode 144, the unfired measuring-electrode lead 191, and the unfired lead insulating layer 192 in an unfired sensor element are formed into the measuring electrode 44, the measuring-electrode lead 91, and the lead insulating layer 92, respectively. The unfired bonding layer 194 and the unfired back-surface bonding layer 197 are formed into the bonding layer 94 (FIG. 6F).

Figure 10A:
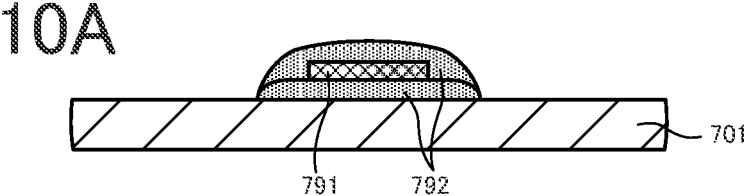
FIGS. 10A to 10D show views illustrating that a sensor element is being manufactured such that an edge portion of an unfired insulating layer 792 and that of an unfired bonding layer 794 contact each other.
Figure 10B:
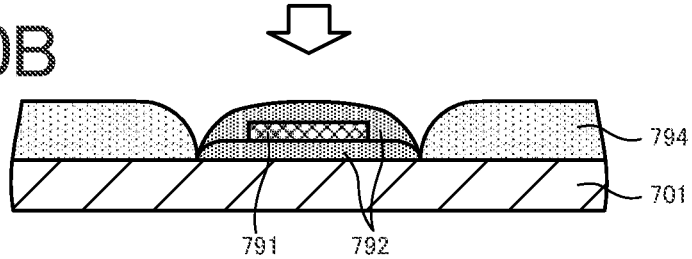
Figure 10C:
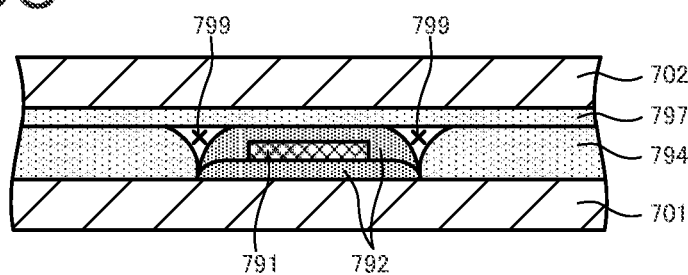
Figure 10D:
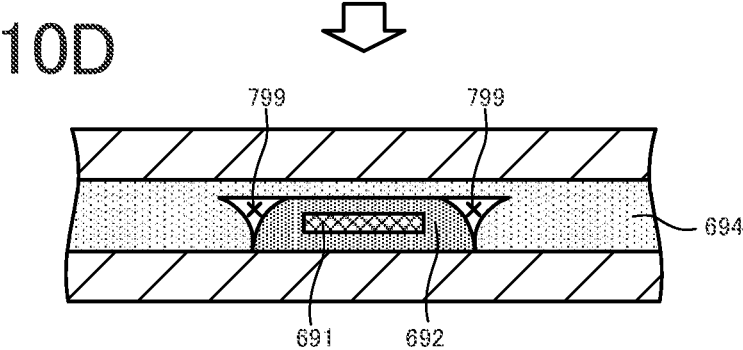

As described above, according to the manufacturing method for the sensor element 101 of this embodiment, in step (c) of the forming step, the unfired bonding layer 194 is formed to provide the overlapping region 195 where the unfired bonding layer 194 overlaps at least part of the edge portion of the unfired lead insulating layer 192 (FIGS. 5C and 6D). In contrast to this embodiment, the following case will be considered. As shown in FIG. 10B, the unfired bonding layer 794 is formed so that the edge portion of the unfired bonding layer 794 contacts (does not overlap) the edge portion of the unfired insulating layer 792. In this case, the gaps 799 may be produced in the multilayer body as shown in FIG. 10C or in the fired sensor element 101 as shown in FIG. 10D. With the presence of the gaps 799 in the sensor element 101, oxygen within the gaps 799 (oxygen contained in air filling the gaps 799, for example) may flow and reach the vicinities of an electrode during the use of the sensor element 101, and the concentration of a specified gas may not be detected with high precision. For example, if oxygen other than that generated by reducing of nitrogen oxide (that is, oxygen which does not originate from a specified gas) flows from the gaps 799 to the vicinity of the measuring electrode 44, the pump current Ip2 or the electromotive force V2 shown in FIG. 1 is changed in accordance with such oxygen. This decreases the detection precision of the NOx concentration, which is detected by using at least one of the pump current Ip2 and the electromotive force V2. A decrease in the detection precision is compensated for if the auxiliary pump cell 50 pumps out oxygen flowing from the gaps 799 to the outside. However, the detection precision remains low at least during a period for which oxygen is not sufficiently pumped out to the outside, such as at the start of the use of the sensor element 101. In this manner, if oxygen flows from the gaps 799 and reaches the vicinity of the measuring electrode 44, the precision in detecting the NOx concentration is decreased at the start of the use of the sensor element 101. That is, the initial stability is decreased. In contrast, in this embodiment, the presence of the overlapping region 195 as shown in FIGS. 5C and 6D makes it less likely to produce gaps between (near the boundary between) the unfired lead insulating layer 192 and the unfired bonding layer 194 after the stacking step (FIG. 6E). It is accordingly less likely to produce gaps between the lead insulating layer 92 and the bonding layer 94 in the fired sensor element 101 (FIG. 6F). It is thus less probable that oxygen in gaps will flow and reach the vicinity of the measuring electrode 44 during the use of the sensor element 101, thereby making it possible to substantially maintain the initial stability of the sensor element 101.

In step (c), the unfired bonding layer 194 is preferably formed so that the maximum value Womax of the width of the overlapping region 195 of the unfired lead insulating layer 192 and the unfired bonding layer 194 will be 20 to 140 µm. With the presence of the overlapping region 195, the maximum value Womax is greater than 0 µm. With the maximum value Womax of 20 µm or greater, it is even less likely to decrease the precision in detecting the concentration of a specified gas in the sensor element 101 (initial stability in this example). With the maximum value Womax of 140 µm or smaller, it is possible to reduce a warpage which may occur in the sensor element 101 during firing due to an increased width of the overlapping region 195, that is, a greater amount of paste applied to part of the green sheet 204. In this embodiment, the overlapping region 195 is disposed on the left side of the sensor element 101 in the left-right direction. With an increased width of the overlapping region 195, the fired sensor element 101 may warp to swell toward the left side. However, a warpage of the fired sensor element 101 is not likely to occur in this embodiment. To reduce the occurrence of warpage in the sensor element 101 more reliably, the maximum value Womax is more preferably 120 µm or smaller. The maximum value Womax is the largest width of the overlapping region 195. In this embodiment, each of the widths Wo1 through Wo4 is uniform, and also, the widths Wo1 through Wo4 are equal to each other, and thus, the widths Wo1 through Wo4=Womax.

In step (c), the unfired bonding layer 194 is preferably formed so that the ratio Womax/Wi of the maximum value Womax [µm] to the width Wi [µm] (see FIG. 5C) of the unfired lead insulating layer 192 in a direction perpendicular to the current flowing direction of the unfired measuring-electrode lead 191 will be 0.04 to 0.29. As the current flowing direction of the unfired measuring-electrode lead 191, the current flowing direction of the longest straight portion (second straight portion 191b in this embodiment) of the unfired measuring-electrode lead 191 is used. Accordingly, in this embodiment, the current flowing direction of the unfired measuring-electrode lead 191 is the longitudinal direction of the sensor element 101, that is, the front-rear direction. The width Wi is a width of the unfired lead insulating layer 192 in the left-right direction perpendicular to the front-rear direction. With the presence of the overlapping region 195, the ratio Womax/Wi is greater than 0 µm. With the ratio Womax/Wi of 0.04 or greater, the precision in detecting the concentration of a specified gas in the sensor element 101 is even less likely to decrease. With the ratio Womax/Wi of 0.29 or smaller, it is possible to reduce a warpage which may occur in the sensor element 101 during firing due to an increased width of the overlapping region 195, that is, a greater amount of paste applied to part of the green sheet 204. To further reduce the occurrence of warpage in the sensor element 101, the ratio Womax/Wi is more preferably 0.24 or smaller. The width Wi is 500 to 650 µm, for example, though it is not limited to this range. The width of the unfired measuring-electrode lead 191 is 200 to 300 µm, for example. The width Wi may be 1.0 to 3.25 times as large as the width of the unfired measuring-electrode lead 191. The width Wi may be 1.1 times or more as large as the width of the unfired measuring-electrode lead 191.

According to the manufacturing method for the sensor element 101 of this embodiment discussed above in detail, in step (c) of the forming step, the unfired bonding layer 194 is formed to overlap at least part of the edge portion of the unfired lead insulating layer 192. This makes it less likely to decrease the precision in detecting the NOx concentration in the sensor element 101 (initial stability). Setting the maximum value Womax to be 20 µm or greater makes it even less likely to decrease the detection precision of the sensor element 101. Setting the maximum value Womax to be 140 µm or smaller can reduce the occurrence of warpage in the sensor element 101 during firing. Setting the ratio Womax/Wi to be 0.04 or greater makes it even less likely to decrease the detection precision of the sensor element 101. Setting the ratio Womax/Wi to be 0.29 or smaller can reduce the occurrence of warpage in the sensor element 101 during firing.

According to the manufacturing method for the sensor element 101, the unfired lead insulating layer 192 formed in step (b) includes the straight portion 193. The straight portion 193 is disposed such that the unfired measuring electrode 144 is not located on a line extending from the straight portion 193 in the longitudinal direction (front-rear direction). In step (c), among the edge portions (left-side edge portion and right-side edge portion) along the longitudinal direction of the straight portion 193, the unfired bonding layer 194 is formed to overlap at least the edge portion (right-side edge portion) of the straight portion 193 closer to the unfired measuring electrode 144. That is, the unfired bonding layer 194 is formed to provide the first overlapping region 195a. As the distance between an electrode and a gap is smaller, oxygen in the gap is more likely to reach the vicinity of the electrode, and the detection precision of the sensor element 101 is more likely to decrease. The unfired bonding layer 194 is formed such that the first overlapping region 195a, which is closer to the unfired measuring electrode 144 than the second overlapping region 195b, is provided. Accordingly, it is less likely to produce gaps near the edge portion of the lead insulating layer 92 closer to the measuring electrode 44. This enhances the effect of suppressing in the detection precision of the sensor element 101.

According to the manufacturing method for the sensor element 101, in step (a), the unfired measuring electrode 144, which will be formed into the measuring electrode 44 after firing, is formed as the unfired electrode. In step (b), the unfired measuring-electrode lead 191, which is connected to the unfired measuring electrode 144 and will be formed into the measuring-electrode lead 91 after firing, is formed as the unfired electrode lead. This makes it less likely to produce a gap between the bonding layer 94 and the lead insulating layer 92 which surrounds the measuring-electrode lead 91 to be connected to the measuring electrode 44. It is thus less probable that oxygen in a gap will flow and reach the vicinity of the measuring electrode 44 during the use of the sensor element 101. If oxygen in a gap flows and reaches the vicinity of the measuring electrode 44, the precision in detecting the concentration of a specified gas is more likely to decrease than when oxygen in a gap flows and reaches the vicinity of another electrode. By forming the unfired bonding layer 194 to overlap at least part of the edge portion of the unfired lead insulating layer 192 which surrounds at least part of the unfired measuring-electrode lead 191, it is even less probable that the precision in detecting the concentration of a specified gas in the sensor element 101 will decrease.

According to the manufacturing method for the sensor element 101, in steps (a) through (c), plural patterns of each of the unfired measuring electrode 144, the unfired measuring-electrode lead 191, the unfired lead insulating layer 192, and the unfired bonding layer 194 are formed on the green sheet 204 so that the patterns, each corresponding to one sensor element 101, are arranged in a predetermined direction (left-right direction) perpendicular to the longitudinal direction (front-rear direction) of the sensor element 101. In the cutting step, the plural unfired sensor elements are cut out from the multilayer body. In the firing step, the plural unfired sensor elements are fired to produce the plural sensor elements 101, thereby making it possible to manufacture the plural sensor elements 101 at one time.

The present invention is not whatsoever restricted to the above-described embodiment and may be carried out in various modes without departing from the technical scope of the present invention.

Figure 7:
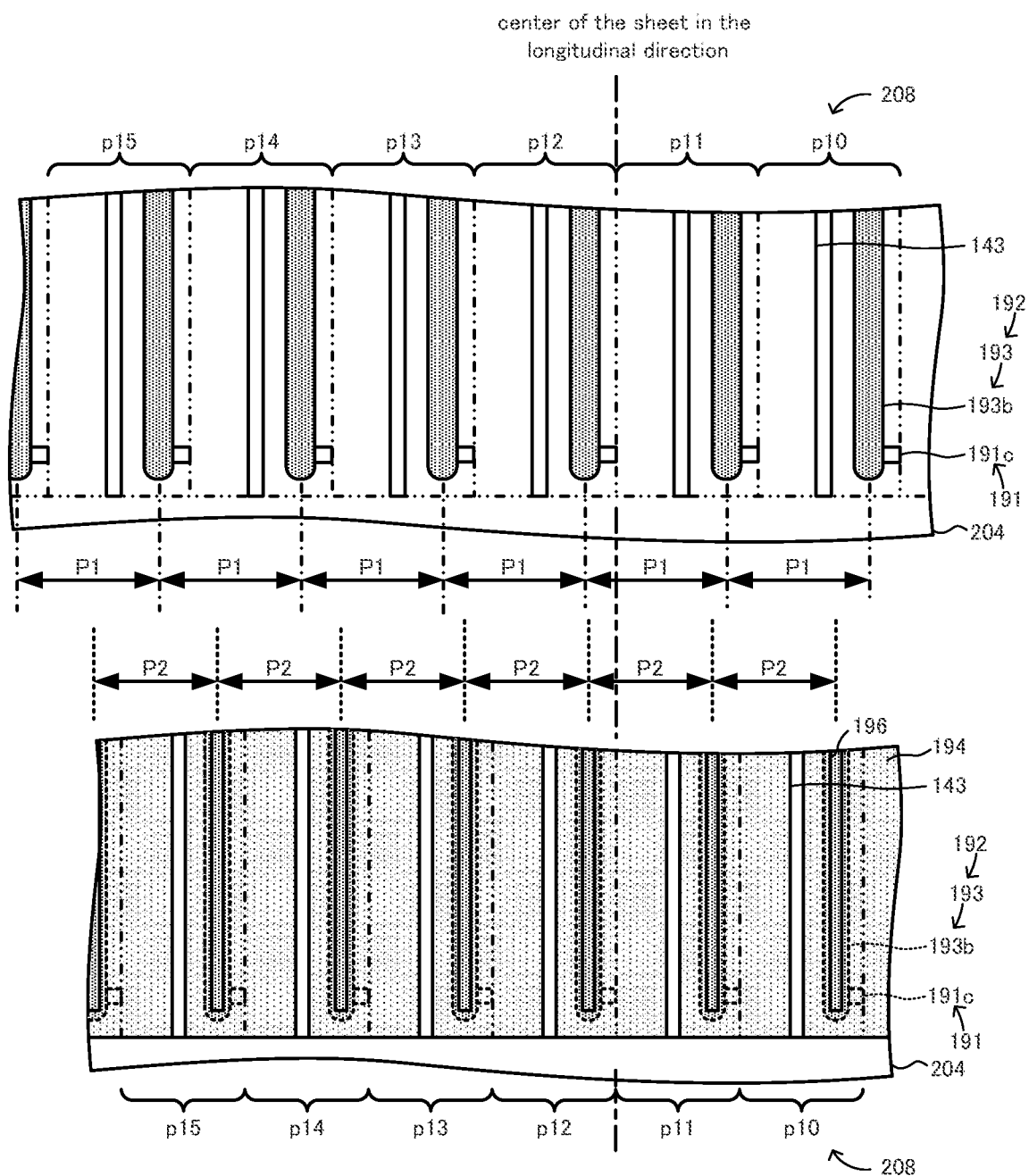
FIG. 7 is a view illustrating a first pitch P1 used for forming an unfired lead insulating layer 192 and a second patch P2 used for forming an unfired bonding layer 194.

In the above-described embodiment, a detailed explanation has not been given of a pitch of plural patterns used for forming a pattern corresponding to one sensor element 101 in each of the device regions 208. This will now be explained below. FIG. 7 is a view illustrating a first pitch P1 used for forming the unfired lead insulating layer 192 and a second patch P2 used for forming the unfired bonding layer 194. FIG. 7 shows part of the device regions p10 through p15 on the green sheet 204 (region on the rear side of the sensor element 101). The upper section of FIG. 7 shows the state immediately after the unfired lead insulating layer 192 (upper insulating layer 193b) is formed (after printing and before drying of the unfired lead insulating layer 192). The lower section of FIG. 7 shows the state immediately after the unfired bonding layer 194 is formed. When various patterns corresponding to one sensor element 101 are formed in each of the device regions 208 arranged in a predetermined direction (left-right direction in FIG. 4) perpendicular to the longitudinal direction of the sensor element 101, the pitches between the patterns in the predetermined direction are basically set to be the same value (first pitch P1 in FIG. 7, for example) no matter which pattern will be formed. However, if, in step (b), plural patterns of the unfired lead insulating layer 192 are formed so that the patterns, each pattern corresponding to one sensor element 101, are arranged in the predetermined direction at the first pitch P1, it is preferable that, in step (c), plural patterns of the unfired bonding layer 194 be formed so that the patterns, each pattern corresponding to one sensor element 101, are arranged in the predetermined direction at the second pitch P2 which is smaller than the first pitch P1. That is, as in the device regions p10 through p15 shown in FIG. 7, if the pitch of the unfired lead insulating layer 192 between adjacent device regions 208 in the predetermined direction is the first pitch P1 (upper section of FIG. 7), it is preferable that the pitch of the unfired bonding layer 194 between adjacent device regions 208 in the predetermined direction be the second pitch P2 (<P1) (lower section of FIG. 7). When plural patterns of the unfired lead insulating layer 192 are formed on the green sheet 204 so that the plural patterns, each corresponding to one sensor element 101, are arranged in the predetermined direction, if the green sheet 204 shrinks after drying, the pitch of the patterns of the unfired lead insulating layer 192 becomes smaller than the first pitch P1 used for forming the patterns. In this case, if the pitch for forming the plural patterns of the unfired lead insulating layer 192 and the pitch for forming the plural patterns of the unfired bonding layer 194 are set to be the same first pitch P1, misregistration occurs between at least some of the plural patterns of the unfired bonding layer 194 and the corresponding patterns of the unfired lead insulating layer 192. For example, it is now assumed that the unfired bonding layer 194 is formed on the green sheet 204 after performing positioning of a screen mask for forming the unfired bonding layer 194 based on the center of the green sheet 204 in the longitudinal direction. In this case, the amount of misregistration between the contracted unfired lead insulating layer 192 and the unfired bonding layer 194 becomes greater as the position of the green sheet 204 is toward the outer side in the longitudinal direction. In FIG. 7, the center of the green sheet 204 in the longitudinal direction is set on a boundary between the device regions p11 and p12. When misregistration occurs, the width of the overlapping region (in particular, the widths Wo1 and Wo2, which are the widths of the overlapping regions along the predetermined direction) of the unfired lead insulating layer 192 and the unfired bonding layer 194 deviates from a target value. This includes a case in which at least one of the first and second overlapping regions 195a and 195b disappears. If the unfired bonding layer 194 is formed by using the first pitch P1 based on the center of the green sheet 204 in the longitudinal direction as shown in FIG. 7, it is displaced outward with respect to the unfired lead insulating layer 192 due to the contraction of the green sheet 204. Hence, it is more likely that the width Wo1 becomes smaller than the target value and the width Wo2 becomes larger than the target value as the device region 208 is positioned farther toward the left side in FIG. 7, that is, as the device region 208 is positioned closer to the device region p22 in FIG. 4. Similarly, it is more likely that the width Wo1 becomes larger than the target value and the width Wo2 becomes smaller than the target value as the device region 208 is positioned farther toward the right side in FIG. 7, that is, as the device region 208 is positioned closer to the device region p1 in FIG. 4. If the width of the overlapping region differs from the target value, for example, if the width of the overlapping region becomes smaller, it is more likely to manufacture sensor elements 101 that fail to sufficiently maintain the precision in detecting the concentration of a specified gas. Conversely, if the width of the overlapping region becomes greater, the above-described effect of reducing the occurrence of warpage in the fired sensor element may not be sufficiently achieved. That is, the yield of the sensor elements 101 is decreased. In contrast, plural patterns of the unfired bonding layer 194 are formed by using the second pitch P2, which is smaller than the first pitch P1 for forming the patterns of the unfired lead insulating layer 192. Then, it is possible to reduce misregistration between the patterns of the unfired bonding layer 194 and those of the unfired lead insulating layer 192 after the green sheet 204 has contracted. This reduces the difference between the actual value of the width of the overlapping region and the target value, thereby making it possible to improve the yield of the sensor elements 101.

The unfired bonding layer 194 in the lower section of FIG. 7 is formed to cover most part of each device region 208 except for the non-forming region 196. The plural patterns of the unfired bonding layer 194 formed in the individual device regions 208 are thus connected (contact) with each other. The pattern of the unfired bonding layer 194 in each device region 208 includes the non-forming region 196 so as to avoid some portions such as the unfired lead insulating layer 192. The pitch of the non-forming region 196 in the predetermined direction serves as the pitch (second pitch P2) of the plural patterns of the unfired bonding layer 194 in the predetermined direction. The second pitch P2 may be determined in the following manner by experiment. By checking how much the unfired lead insulating layer 192 formed by using the first pitch P1 has contracted after drying, the second pitch P2 may be set to be the same value as the pitch of the unfired lead insulating layer 192 after drying (pitch for forming the unfired bonding layer 194). For example, the second pitch P2 may be a length [mm] which is 99% or greater and smaller than 100% of the first pitch P1. The second pitch P2 may be 99.5% or greater or 99.9% or greater of the first pitch P1. As in the above-described embodiment, if the unfired lead insulating layer 192 is formed separately over multiple times (by forming the lower insulating layer 193a and the upper insulating layer 193b), the pitch used for forming the final layer (pitch for forming the upper insulating layer 193b in this example) is used as the first pitch P1. As in the above-described embodiment, if the unfired bonding layer 194 is formed separately over multiple times (by forming the lower bonding layer 194a and the upper bonding layer 194b), the pitch used for forming the overlapping region 195 (in particular, the first overlapping region 195a and the second overlapping region 195b having the width along the predetermined direction) (pitch for forming the upper bonding layer 194b in this example) is used as the second pitch P2. In this case, the pitch used for forming any of the layers for forming the unfired bonding layer 194 is preferably smaller than the first pitch P1. For example, the second pitch P2 may be used every time a layer is formed for the unfired bonding layer 194. If the upper bonding layer 194b is formed after the lower bonding layer 194a is dried, the contraction caused by drying the lower bonding layer 194a is also taken into account, and the pitch for forming the upper bonding layer 194b may be set to be smaller than that for forming the lower bonding layer 194a. As in the formation of the unfired bonding layer 194, when patterns are formed on the same green sheet 200, the pitch of a pattern to be formed later may be set to be smaller. For example, when the lower insulating layer 193a, the unfired measuring-electrode lead 191, and the upper insulating layer 193b are formed in this order, the pitch of a pattern of one of these elements to be formed later may be set to be smaller. However, if the width of the lower insulating layer 193a and the upper insulating layer 193b is sufficiently greater than that of the unfired measuring-electrode lead 191, misregistration among the forming positions of the lower insulating layer 193a, the unfired measuring-electrode lead 191, and the upper insulating layer 193b caused by the contraction during drying does not significantly influence the characteristics of the sensor element 101, for example. From this point of view, reducing the misregistration between the unfired lead insulating layer 192 and the unfired bonding layer 194 is more effective in improving the yield of the sensor elements 101 than reducing misregistration between other patterns.

During the drying of the formed unfired lead insulating layer 192, the green sheet 204 contracts, not only in the longitudinal direction (left-right direction in FIGS. 4 and 7), but also in the widthwise direction (top-bottom direction in FIGS. 4 and 7). Accordingly, if patterns, each pattern corresponding to one sensor element 101, are formed to be arranged in plural rows (two rows in FIG. 4) in a direction perpendicular to the predetermined direction, the pitch of the patterns arranged in the direction perpendicular to the predetermined direction may also be adjusted, that is, the pitch of the unfired bonding layer 194 may be set to be smaller than that of the unfired lead insulating layer 192. For example, the pitch (in the top-bottom direction of FIG. 4) between the patterns formed in the device regions p1 through p22 in FIG. 4 and those formed in the device regions p23 through p44 in FIG. 4 for forming the unfired bonding layer 194 may be set to be smaller than that used for forming the unfired lead insulating layer 192. This can decrease the possibility that the width of the overlapping region (in particular, the widths Wo3 and Wo4 of the overlapping regions in the direction perpendicular to the predetermined direction) of the unfired lead insulating layer 192 and the unfired bonding layer 194 will deviate from a target value. As a result, the yield of the sensor elements 101 can be improved. However, the amount of contraction of the green sheet 204 in the longitudinal direction is greater than that in the widthwise direction. Setting of the second pitch P2 of the patterns arranged in the predetermined direction in FIG. 7 to be smaller than the first pitch P1 is more effective in improving the yield of the sensor elements 101.

In the above-described embodiment, the unfired bonding layer 194 is formed such that the overlapping region 195 has the first through fourth overlapping regions 195a through 195d. However, the formation of the unfired bonding layer 194 is not restricted to this arrangement. The unfired bonding layer 194 may be formed in a different manner if it overlaps at least part of the edge portion of the unfired lead insulating layer 192. That is, the unfired bonding layer 194 may be formed at least to provide the overlapping region 195. For example, the provision of the fourth overlapping region 195d may be omitted. At least the first and third overlapping regions 195a and 195c may be provided. As stated above, as the distance between an electrode and a gap is smaller, oxygen in the gap is more likely to reach the vicinity of the electrode. Hence, among the first through fourth overlapping regions 195a through 195d, the provision of at least the first overlapping region 195a is preferable, then, the provision of the third overlapping region 195c is preferable, and then, the provision of the second overlapping region 195b is preferable. Alternatively, at least the third overlapping region 195c may be provided.

In the above-described embodiment, the widths Wo1 through Wo4 of the first through fourth overlapping regions 195a through 195d are the same. However, one or more of the widths Wo1 through Wo4 may be different from the rest of the widths Wo1 through Wo4. The width Wo1 of the first overlapping region 195a is substantially uniform at any position in the front-rear direction. However, this is only an example. For example, the width Wo1 of the first overlapping region 195a may be larger at a position closer to the unfired measuring electrode 144 (toward the front side) and may be smaller at a position farther away from the unfired measuring electrode 144 (toward the rear side). The average value of the width Wo1 (average value of the widths of the first overlapping region 195a at plural positions in the front-rear direction) may be 20 to 140 μm. The width Wo1 of the first overlapping region 195a may be in a range of 20 to 140 μm at any position in the front-rear direction. The second through fourth overlapping regions 195b through 195d may be modified in a similar manner.

In the above-described embodiment, the ratio Womax/Wi is preferably 0.04 to 0.29. Alternatively, the ratio Wo12max/Wi of the maximum value Wo12max [μm] of the widths Wo1 and Wo2 to the width Wi may be 0.04 to 0.29. The maximum value Wo12max is the maximum value of the widths of the first and second overlapping regions 195a and 195b. In other words, the maximum value Wo12max is the width of the overlapping portion of the unfired bonding layer and the edge portion of the unfired lead insulating layer 192 along the longitudinal direction of the straight portion 193.

In the above-described embodiment, in step (a), the unfired measuring electrode 144, which will be formed into the measuring electrode 44 after firing, is formed as the unfired electrode. In step (b), the unfired measuring-electrode lead 191, which is connected to the unfired measuring electrode 144 and will be formed into the measuring-electrode lead 91 after firing, is formed as the unfired electrode lead. However, these are only examples. The unfired electrode lead formed in step (b) may be any unfired electrode lead to be sandwiched between green sheets in a multilayer body. By providing an overlapping region between the unfired lead insulating layer which surrounds such an unfired electrode lead and the unfired bonding layer, oxygen within a gap is less likely to flow and reach the vicinity of an electrode to be connected to the unfired electrode lead. It is thus possible to suppress the precision in detecting the concentration of a specified gas in the sensor element. For example, the unfired electrode lead to be connected to the unfired electrode, which will be formed into the inner pump electrode 22 or the auxiliary pump electrode 51 after firing, will now be considered. If an overlapping region is provided between the unfired bonding layer and the unfired lead insulating layer which surrounds the unfired electrode lead, the effect in maintaining the initial stability of the sensor element 101 is achieved, as in the above-described embodiment. If oxygen flows from a gap to the vicinity of the inner pump electrode 22 or the auxiliary pump electrode 51, the detection precision of the sensor element 101 may become low and remain the same until the pump cell (main pump cell 21 or auxiliary pump cell 50) including the corresponding one of the inner pump electrode 22 and the auxiliary pump electrode 51 finishes pumping out oxygen. However, the provision of the overlapping region makes it less likely to decrease the detection precision of the sensor element 101. Steps (a) through (c) may be performed on each of the plural electrodes (at least two of the measuring electrode 44, the inner pump electrode 22, and the auxiliary pump electrode 51, for example) and the electrode leads connected to the respective electrodes. With this arrangement, oxygen is less likely to flow from a gap to the vicinities of such plural electrodes, thereby enhancing the effect in maintaining the detection precision of the sensor element 101.

In the above-described embodiment, the single green sheet 204 includes the forty-four device regions 208, as shown in FIG. 4. However, the number and the arrangement of device regions 208 are not restricted to those described above. For example, one green sheet may have one device region 208.

In the above-described embodiment, the sensor element 101 detects the NOx concentration as the concentration of a specified gas contained in a measurement-object gas. However, this is only an example. For example, the sensor element 101 may detect the oxygen concentration as the concentration of a specified gas.

EXAMPLES

Examples of specifically fabricated sensor elements will be discussed below as examples. Second through sixth experiment examples correspond to examples of the present invention, and a first experiment example corresponds to a comparative example. However, the present invention is not restricted to the following examples.

First Experiment Example

According to the manufacturing method for the sensor element 101 of the embodiment discussed with reference to FIGS. 4 through 6, the sensor elements 101 shown in FIG. 1 were fabricated and were used as the first experiment example. In the first experiment example, however, in step (c), the edge portion of the unfired lead insulating layer 192 and that of the unfired bonding layer 194 were in contact with each other without providing the overlapping region 195 therebetween. That is, the widths Wo1 through Wo4=the maximum value Womax=0 μm, and the ratio Womax/Wi was 0 (all of them were target values, that is, the set values). The dimensions of the manufactured sensor elements 101 were as follows: the length in the front-rear direction was 67.5 mm, the width in the left-right direction was 4.25 mm, and the thickness in the top-bottom direction was 1.45 mm. To fabricate the sensor elements 101, green sheets 200 were formed by mixing zirconia particles to which 4 mol % of yttria, which was a stabilizer, was added, an organic binder, and an organic solvent and by molding the resulting mixture into a tape-like shape. As the conductive paste for the unfired measuring-electrode lead 191, a paste made of a mixture of 11.2 mass % of zirconia particles to which 4 mol % of yttria, which was a stabilizer, was added, 60 mass % of platinum, an organic binder, and an organic solvent was used. As the insulating paste for the lead insulating layer 92, alumina powder and a binder solution were mixed at a weight ratio of 1:2, and the resulting mixture was adjusted so that the viscosity thereof at room temperature would be 40 [Pa·s]. As the paste for the bonding layer 94, zirconia particles to which 4 mol % of yttria, which was a stabilizer, was added, an organic binder, and an organic solvent were mixed, and the resulting mixture was adjusted so that the viscosity thereof at room temperature would be 20 [Pa·s]. The thickness of the unfired measuring-electrode lead 191 was 7 to 17 μm, and the thickness of the second straight portion 191b of the unfired measuring-electrode lead 191 was 9 to 15 μm. The width Wi of the unfired lead insulating layer 192 was 490 μm, and the total thickness of the lower insulating layer 193a and the upper insulating layer 193b was 30 μm. The total thickness of the lower bonding layer 194a and the upper bonding layer 194b was 35 μm. The thickness of the unfired back-surface bonding layer 197 was 10 μm. As shown in FIG. 7, the second pitch P2 of the unfired bonding layer 194 was set to be smaller than the first pitch P1 of the unfired lead insulating layer 192 so that the actual values of the widths Wo1 through Wo4 would substantially coincide with the target value. More specifically, the unfired lead insulating layer 192 (lower insulating layer 193a and upper insulating layer 193b) and the unfired measuring-electrode lead 191 were formed by using the first pitch P1 of 5.27 mm. The unfired bonding layer (lower bonding layer 194a and upper bonding layer 194b) was formed by using the second pitch P2 of 5.267 mm. For forming the patterns of the lower insulating layer 193a, the unfired measuring-electrode lead 191, the upper insulating layer 193b, the lower bonding layer 194a, and the second overlapping region 195b in this order, drying was conducted every time one pattern was formed.

Second Through Sixth Experiment Examples

The sensor elements 101 were fabricated in a manner similar to the first experiment example, except that the target value of the maximum value Womax and that of the ratio Womax/Wi were varied by changing the configuration of the non-forming region 196 in a screen mask for forming the unfired bonding layer 194. The fabricated sensor elements 101 were used as second through sixth experiment examples. More specifically, in the second experiment example, the widths Wo1 through Wo3=the maximum value Womax=30 μm, and the ratio Womax/Wi was set to be 0.06. In the third experiment example, the widths Wo1 through Wo3=the maximum value Womax=60 μm, and the ratio Womax/Wi was set to be 0.12. In the fourth experiment example, the widths Wo1 through Wo3=the maximum value Womax=100 μm, and the ratio Womax/Wi was set to be 0.20. In the fifth experiment example, the widths Wo1 through Wo3=the maximum value Womax=130 μm, and the ratio Womax/Wi was set to be 0.27. In the sixth experiment example, the widths Wo1 through Wo3=the maximum value Womax=150 μm, and the ratio Womax/Wi was set to be 0.31. In all the second through sixth experiment examples, the overlapping region 195 had no fourth overlapping region 195d. Each of the first pitch P1 and the second pitch P2 in the second through sixth experiment examples was set to be the same value as that in the first experiment example.

[Evaluations Regarding Initial Stability]

Concerning the first through sixth experiment examples, the detection precision of the sensor elements 101 regarding a measurement-object gas was evaluated, and more specifically, the initial stability of the sensor elements 101 was evaluated. Evaluations were conducted as follows. To raise the temperature of the heater 72 to a predetermined temperature, a voltage was first applied to the heater unit 70 to cause a current to flow through the heater 72, and nitrogen was supplied to the gas passage. Then, the cells 21, 41, 50, and 80 through 83 were started to drive. After the lapse of a certain period of time (240 seconds) after starting to drive the cells 21, 41, 50, and 80 through 83, the values of the NOx concentration (values of the pump current Ip2) were measured. Measurements were made for all the forty-four sensor elements 101 fabricated in each of the first through sixth experiment examples, and the average and the standard deviation σ of the values of the pump current Ip2 were found for each of the first through sixth experiment examples. When the average value of the pump current Ip2 was 0.065 μA or smaller, the initial stability was found to be good (A), and when the average value of the pump current Ip2 exceeded 0.065 μA, the initial stability was found to be poor (C). The gas supplied to the gas passage was nitrogen which did not contain oxygen. Hence, the pump current Ip2 would ideally be 0 μA, and if oxygen was flown from a gap within the sensor element 101 to an electrode, the pump current Ip2 would be increased.

[Evaluations Regarding Amount of Warpage in Sensor Element]

The amounts of warpage occurred in the sensor elements 101 of the first through sixth experiment examples were measured. Measurements were made for all the forty-four sensor elements 101 fabricated in each of the first through sixth experiment examples, and the average and the standard deviation σ of the amounts of warpage were found for each of the first through sixth experiment examples. When the average amount of warpage was 240 μm or smaller, the evaluation result was set to be very good (A). When the average amount of warpage exceeded 240 μm and was 350 μm or smaller, the evaluation result was set to be good (B). When the average amount of warpage exceeded 350 μm, the evaluation result was set to be poor (C).

Figure 8:
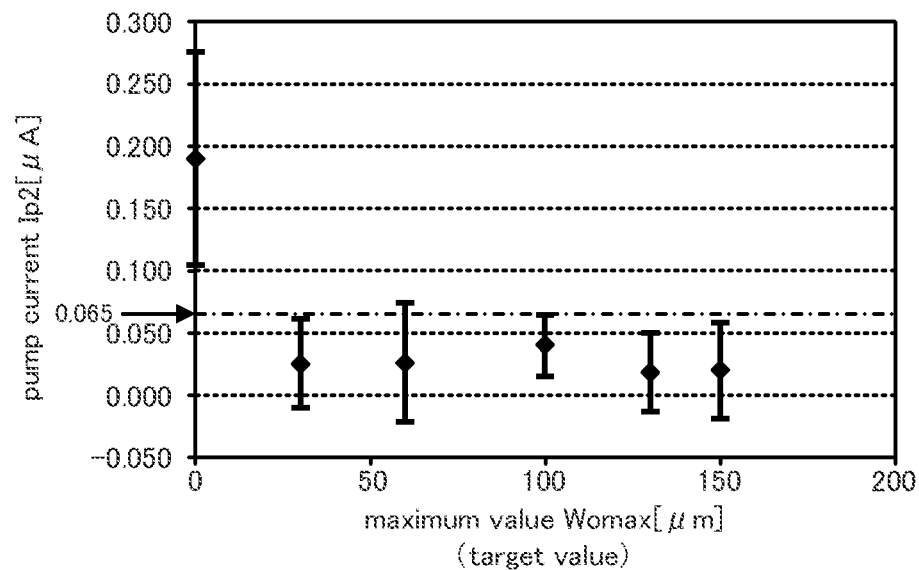
FIG. 8 is a graph illustrating plotting of maximum values Womax and pump current values Ip2 according to first through sixth experiment examples.
Figure 9:
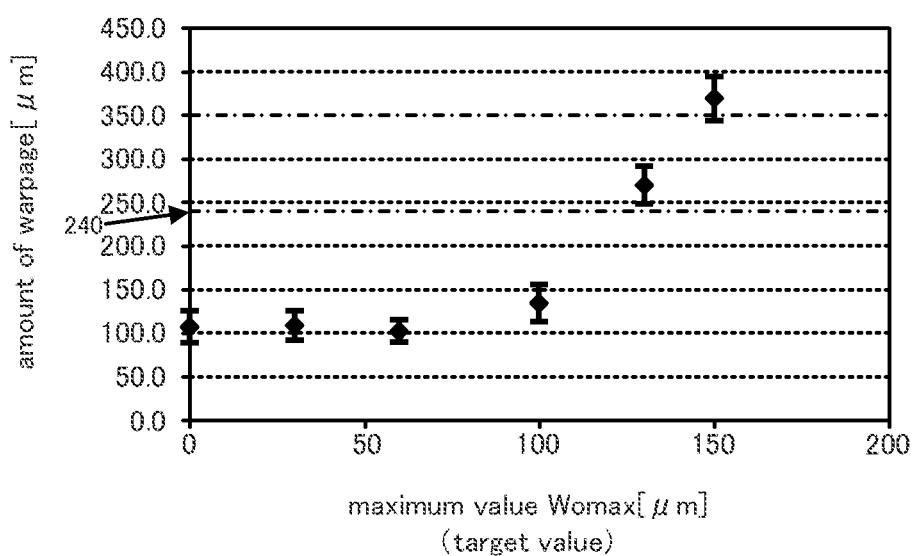
FIG. 9 is a graph illustrating plotting of maximum values Womax and warpage amounts according to the first through sixth experiment examples.

The target value of the maximum value Womax, the target value of the ratio Womax/Wi, the average value of the pump current Ip2, the standard deviation of the pump current Ip2, the evaluation of the initial stability, the average amount of warpage, the standard deviation of the amount of warpage, and the evaluation of the amount of warpage according to each of the first through sixth experiment examples are shown in Table 1. FIG. 8 is a graph illustrating plotting of the target values of the maximum value Womax and the values of the pump current Ip2 according to the first through sixth experiment examples. FIG. 9 is a graph illustrating plotting of the target values of the maximum value Womax and the amounts of warpage according to the first through sixth experiment examples. In FIGS. 8 and 9, the rhombus represents the average value, and the horizontal bars above and under the rhombus indicate the values represented by the average value ±σ.

TABLE 1

|  | EXPERIMENTAL EXAMPLE | | | | | |
| --- | --- | --- | --- | --- | --- | --- |
|  | 1 | 2 | 3 | 4 | 5 | 6 |
| MAXIMUM VALUE Womax [μm](TARGET VALUE) | 0 | 30 | 60 | 100 | 130 | 150 |
| RATIO Womax/Wi (TARGET VALUE) | 0.00 | 0.06 | 0.12 | 0.20 | 0.27 | 0.31 |
| AVERAGE VALUE OF Ip2 [μmA] | 0.190 | 0.025 | 0.026 | 0.040 | 0.018 | 0.020 |
| STANDARD DEVIATION OF Ip2σ [μmA] | 0.086 | 0.036 | 0.048 | 0.025 | 0.032 | 0.039 |
| EVALUATION OF THE INITIAL STABILITY | C | A | A | A | A | A |
| AVERAGE AMOUNT OF WARPAGE [μm] | 107.6 | 109.3 | 102.8 | 134.9 | 270.3 | 370.0 |
| STANDARD DEVIATION OF THE AMOUNT OF WARPAGE σ [μm] | 17.5 | 16.3 | 12.3 | 20.7 | 21.8 | 25.1 |
| EVALUATION OF THE AMOUNT OF WARPAGE | A | A | A | A | B | C |

Table 1 and FIG. 8 showed that, upon comparing the second through sixth experiment examples in which the target values of the maximum value Womax exceeded 0 with the first experiment example in which the overlapping region 195 was not provided, that is, the target value of the maximum value Womax was 0, the values of the pump current Ip2 in all the second through sixth experiment examples were reduced, and the high initial stability was achieved. Table 1 and FIG. 8 also showed that the standard deviations of the pump current Ip2 of the second through sixth experiment examples were smaller than that of the first experiment example. Table 1 and FIG. 9 showed that, as the target value of the maximum value Womax was smaller, the amount of warpage tended to be smaller. Table 1 and FIG. 9 also showed that the amounts of warpage in the first through fifth experiment examples in which the target values of the maximum value Womax were 130 μm or smaller were smaller than that in the sixth experiment example in which the target values of the maximum value Womax exceeded 130 μm. The amounts of warpage in the first through fourth experiment examples in which the target values of the maximum value Womax were 100 μm or smaller were smaller than that of the fifth experiment example. These results show that, from the viewpoint of suppressing in the detection precision of the sensor element 101, the maximum value Womax may be preferably 20 μm or greater, and more preferably, 30 μm or greater. Likewise, from the viewpoint of suppressing in the detection precision of the sensor element 101, the ratio Womax/Wi may be preferably 0.04 or greater, and more preferably, 0.06 or greater. From the viewpoint of reducing the occurrence of warpage in the sensor element 101, the maximum value Womax may be preferably 140 μm or smaller, more preferably, 130 μm or smaller, and even more preferably, 120 μm or smaller. The maximum value Womax may be even more preferably 100 μm or smaller, yet more preferably, 90 μm or smaller, even yet more preferably 70 μm or smaller, and even yet more preferably 60 μm or smaller. From the viewpoint of reducing the occurrence of warpage in the sensor element 101, the ratio Womax/Wi may be preferably 0.29 or smaller, more preferably, 0.27 or smaller, and even more preferably, 0.24 or smaller. The ratio Womax/Wi may be particularly preferably 0.20 or smaller, yet more preferably, 0.18 or smaller, even yet more preferably 0.14 or smaller, and even yet more preferably 0.12 or smaller.

Concerning the first experiment example, the plural sensor elements 101 fabricated at the positions in the device regions p1, p11, and p22 shown in FIG. 4 were cut off and checked for gaps between the lead insulating layer 92 and the bonding layer 94 in cross section, and if any, the sizes of the gaps. The average width of the gaps was 46.7 μm. The widths of the gaps were measured specifically in the following manner. The straight portion 193 of the lead insulating layer 192 was first observed in cross section similar to that shown in FIGS. 6A to 6F. Among the gaps found in cross section, the total width of the gaps at the left and right sides (corresponding to the left and right sides in FIGS. 6A to 6F) of the straight portion 193 was measured. Then, the value of half the total width was set to be the width of the gaps of the sensor element 101. For the third experiment example, the average width of the gaps was similarly calculated and found to be 3.8 μm. It was thus validated that gaps between the lead insulating layer 92 and the bonding layer 94 were less likely to occur in the third experiment example than in the first experiment example. In the third experiment example, no gaps were found in some sensor elements 101 in cross section (that is, the width of gaps was 0 μm). In the first experiment example, however, gaps were found in all the sensor elements 101 in cross section.

What is claimed is:

1. A manufacturing method for a sensor element which detects the concentration of a specified gas contained in a measurement-object gas, comprising:
   a preparing step of preparing a plurality of green sheets made of ceramic, which is an oxygen-ion-conductive solid electrolyte, as a main constituent;
   a forming step including:
      a step (a) of forming an unfired electrode made of a conductive paste on one of the plurality of green sheets,
      a step (b) of forming an unfired electrode lead and an unfired lead insulating layer on the same green sheet as in the step (a), the unfired electrode lead made of a conductive paste and to be connected to the unfired electrode, the unfired lead insulating layer made of an insulating paste and to surround at least part of the unfired electrode lead, and
      a step (c) of forming an unfired bonding layer made of a bonding paste so as to fill at least part of a region without the unfired lead insulating layer on the green sheet subjected to the step (b) and so as to overlap at least part of an edge portion of the unfired lead insulating layer;
   a stacking step of stacking the plurality of green sheets including the green sheet subjected to the steps (a) through (c) so as to form a multilayer body in which the unfired electrode lead is sandwiched between green sheets;
   a cutting step of cutting out an unfired sensor element from the multilayer body; and
   a firing step of firing the unfired sensor element to produce a sensor element including an electrode formed from the unfired electrode, an electrode lead formed from the unfired electrode lead, a lead insulating layer formed from the unfired lead insulating layer, and a bonding layer formed from the unfired bonding layer.

2. The manufacturing method for a sensor element according to claim 1, wherein, in the step (c), the unfired bonding layer is formed so that a maximum value Womax of a width of an overlapping region of the unfired lead insulating layer and the unfired bonding layer will be 20 to 140 µm.

3. The manufacturing method for a sensor element according to claim 1, wherein, in the step (c), the unfired bonding layer is formed so that a ratio Womax/Wi of a maximum value Womax [µm] of a width of an overlapping region of the unfired lead insulating layer and the unfired bonding layer to a width Wi [µm] of the unfired lead insulating layer in a direction perpendicular to a current flowing direction of the unfired electrode lead will be 0.04 to 0.29.

4. The manufacturing method for a sensor element according to claim 1, wherein:
the unfired lead insulating layer formed in the step (b) includes a straight portion, the straight portion being disposed such that the unfired electrode is not located on a line extending from the straight portion in a longitudinal direction; and
in the step (c), the unfired bonding layer is formed to overlap, among edge portions of the straight portion along the longitudinal direction, at least an edge portion of the straight portion positioned closer to the unfired electrode.

5. The manufacturing method for a sensor element according to claim 1, wherein:
in the step (a), an unfired measuring electrode, which will be formed into a measuring electrode after firing, is formed as the unfired electrode; and
in the step (b), an unfired measuring-electrode lead, which is connected to the unfired measuring electrode and will be formed into a measuring-electrode lead after firing, is formed as the unfired electrode lead.

6. The manufacturing method for a sensor element according to claim 1, wherein:
in the steps (a) through (c), a plurality of patterns of each of the unfired electrode, the unfired electrode lead, the unfired lead insulating layer, and the unfired bonding layer are formed on the green sheet so that the patterns, each pattern corresponding to one sensor element, are arranged in a predetermined direction perpendicular to a longitudinal direction of the sensor element;
in the cutting step, a plurality of the unfired sensor elements are cut out from the multilayer body; and
in the firing step, the plurality of the unfired sensor elements are fired to produce a plurality of the sensor elements.

7. The manufacturing method for a sensor element according to claim 6, wherein:
in the step (b), the plurality of patterns of the unfired lead insulating layer are formed so that the patterns, each pattern corresponding to one sensor element, are arranged in the predetermined direction at a first pitch; and
in the step (c), the plurality of patterns of the unfired bonding layer are formed so that the patterns, each pattern corresponding to one sensor element, are arranged in the predetermined direction at a second pitch, the second pitch being smaller than the first pitch.

* * * * *